United States Patent [19]
Toukatly et al.

[11] Patent Number: 5,882,876
[45] Date of Patent: *Mar. 16, 1999

[54] MALIGNANT CELL TYPE MARKERS OF THE INTERIOR NUCLEAR MATRIX

[75] Inventors: Gary Toukatly, Amhurst, N.H.; Graham P. Lidgard, Wellesley, Mass.

[73] Assignee: Matritech, Inc., Newton, Mass.

[ * ] Notice: The term of this patent shall not extend beyond the expiration date of Pat. No. 5,783,403.

[21] Appl. No.: 483,924

[22] Filed: Jun. 7, 1995

Related U.S. Application Data

[63] Continuation of Ser. No. 195,487, Feb. 14, 1994, Pat. No. 5,783,403, which is a continuation of Ser. No. 901,701, Jun. 22, 1992, abandoned.

[51] Int. Cl.$^6$ .................... G01N 33/574; G01N 33/53; G01N 33/48; C07K 16/00
[52] U.S. Cl. .................... 435/7.23; 435/7.1; 436/63; 436/64; 530/387.7; 530/388.8
[58] Field of Search .................... 424/138.1, 139.1, 424/155.1; 435/7.23, 7.1; 530/388.8, 387.7, 389.7; 436/63, 64

[56] References Cited

U.S. PATENT DOCUMENTS

| | | | |
|---|---|---|---|
| 4,806,463 | 2/1989 | Goodchild et al. | 435/5 |
| 4,885,236 | 12/1989 | Penman et al. | 435/6 |
| 5,098,890 | 3/1992 | Gewirtz et al. | 514/44 |
| 5,273,877 | 12/1993 | Fey et al. | 435/6 |

FOREIGN PATENT DOCUMENTS

| | | |
|---|---|---|
| WO87/03910 | 7/1987 | WIPO . |
| 91 17266 | 11/1991 | WIPO . |
| WO93/09437 | 5/1993 | WIPO . |

OTHER PUBLICATIONS

Salden et al., "Anti–nuclear matrix antibodies in mixed connective tissue disease" (1982) Eur. J. of Immunology, 12:783–786.
Seaver, "Monoclonal Antibodies in Industry: More Difficult Than Originally Thought" (1994) Gen. Engineering News, 14(14):10 and 21.
News Release; "Clinical Utility of Matritech's Bladder Cancer Test Reported in August Issue of Journal of Urology"; Jul. (1996).
Keesee, et al.; "Utilization of Nuclear Matrix Proteins for Cancer Diagnosis"; *Critical Reviews in Eukaryotic Gene Expression*; 6(2&3):189–124 (1996).
Todorov, et al.; "Detection of the 125–kDa Nuclear Protein Mitotin in Centrosomes, the Poles of the Mitotic Spindle, and the Midbody"; *Experimental Cell Research*; 199:398–401 (1992).
Tousson, "Centrophilin: A Novel Mitotic Spindle Protein Involved in Microtubule Nucleation"; *The J. of Cell Biology*; 112 (No. 3):427–440 (1991).
Whitfiled et al.; "Cloning of a Gene Encoding an Antigen Associated with the Centrosome in Drosophila"; *J. of Cell Science*; 89:467–480 (1988).
Kallajoli et al.; "Ability to Organize Microtubules in Taxol–Treated Mitotic PtK$_2$ Cells Goes with the SPN Antigen and Not With the Centrosome"; *J. of Cell Science*; 102:91–102 (1992).
Nickerson et al.; "A Normally Masked Nuclear Matrix Antigen That Appears at Mitosis on Cytoskeleton Filaments Adjoining Chromosomes, Centrioles, and Midbodies"; *The J. of Cell Biology*; 116 (No. 4):977–987 (Feb. 1992).
Stuurman et al.; "A Monoclonal Antibody Recognizing Nuclear Matrix–Associated Nuclear Bodies"; *J. of Cell Science*; 101:773–784 (1992).
Yang et al.; "The Nuclear–Mitotic Apparatus Protein is Important in the Establishment and Maintenance of the Bipolar Mitotic Spindle Apparatus"; *Molecular Biology of the Cell*; 3:1259–1267 (Nov. 1992).
Maekawa et al.; "Identification of a Minus End–Specific Microtubule–Associated Protein Located at the Mitotic Poles in Cultured Mammalian Cells"; *European J. of Cell Biology*; 54:255–267 (1991).
Thibodeau et al.; "Monoclonal Antibody CC–3 Recognizes Phosphoproteins in Interphase and Mitotic Cells"; *Experimental Cell Research*; 195:145–153 (1991).
Kallajoki, et al.; "A 210 kD nuclear matrix protein is a functional part of the mitotic spindle; a microinjection study using SPN monoclonal antibodies;" *EMBO J.*; 10:3351–3362 (1991).
Briggman et al.; "Detection of nuclear matrix protein in the urine of patients with transitional cell carcinoma," poster presented at NCI Conference on Chemoprevention of Premalignant and Early Malignant Lesions of the Bladder, Toas, New Mexico, Jul. 29–Aug. 2, 1992.
Compton, et al., "Identification of Novel Centromere/Kinetochore–associated Proteins Using Monoclonal Antibodies Generated Against Human Mitotic Chromosome Scaffolds"; *The J. of Cell Biology*; 112 (No. 6):1083–1097 (Mar. 1991).
Harlow et al. (1988) "Antibodies: A Laboratory Manual," *Cold Spring Harbor Laboratory*, p. 27.
Miller et al., "Release of Nuclear Matrix Proteins During Apoptotic Cell Death", *J. Cell Biology*, 115:314A (1991) (Abstract).
Miller et al., "Detection of Nuclear Matrix Proteins in Serum From Cancer Patients", *Cancer Research*, 52(2):422–427 (1992).
Sambrook et al., "Molecular Cloning", *Cold Spring Harbor Lab Press*, p. 739 (1989).
Oeller et al., "Rev. Inhibition of Tom. Fruit Senescence by Antisense RNA", *Science*, 254:437–439 (Oct. 1991).
Compton et al., *J. of Cell Biology*, 116:No. 6, 1395–1408, (Mar. 1992).
Fey et al., *Critical Reviews*, 1:Issue 2, 127–143, (1991).
Yang et al., *J. of Cell Biology*, 116:No. 6, 1303–1317 (Mar. 1992).
Lyderson et al., *Cell*, 22:489–492, (Nov. 1980).

*Primary Examiner*—Sheela Huff
*Assistant Examiner*—Yuonne Eyler
*Attorney, Agent, or Firm*—Testa, Hurwitz & Thibeault, LLP

[57] ABSTRACT

Disclosed are genetic sequences and their encoded amino acid sequences for two interior nuclear matrix proteins useful as markers of malignant cell types. Primary and secondary structure analysis of the proteins is presented as well as means for their recombinant production, and compositions and methods for the use of these markers in clinical assays and cancer therapies.

28 Claims, 2 Drawing Sheets

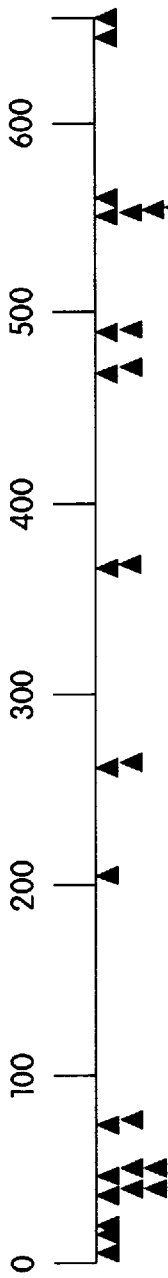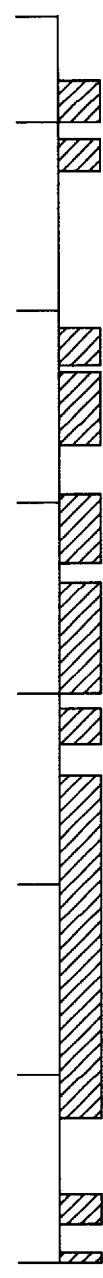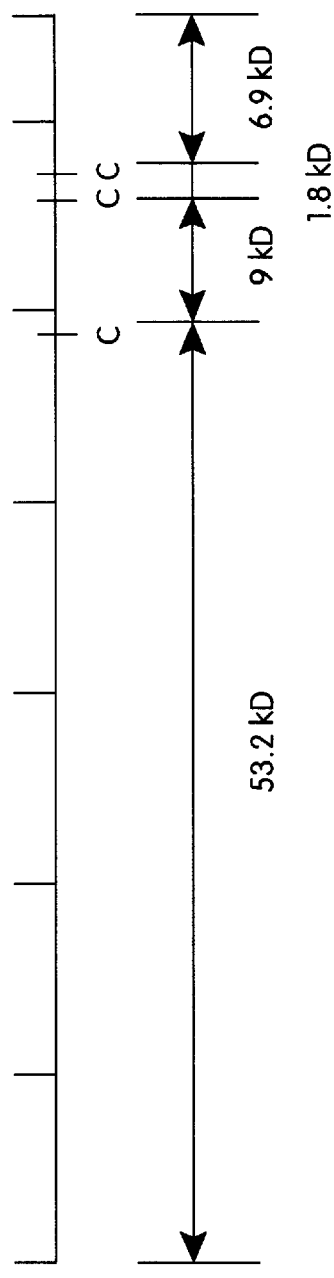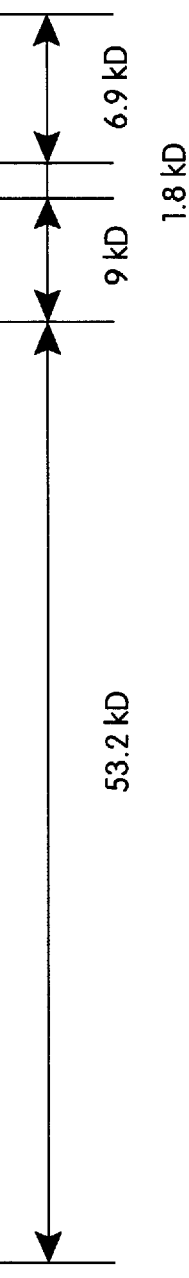

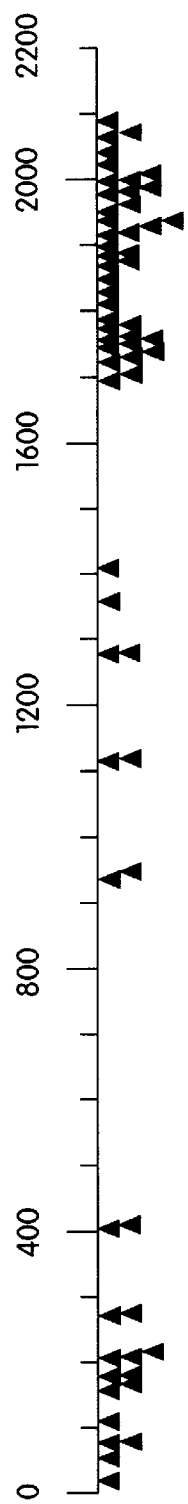
Fig. 2A
Fig. 2B

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 2360 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: HOMO SAPIENS
        ( F ) TISSUE TYPE: CERVIX TUMOR ( i x ) FEATURE:
        ( A ) NAME/KEY: CDS
        ( B ) LOCATION: 94..2010

( x i ) SEQUENCE DESCRIPTION: SEQ ID NO:1:

```
GAGATGGTTC  TTGGTCCTGC  AGCTTATAAT  GTTCCATTGC  CAAAGAAATC  GATTCAGTCG                60

GGTCCACTAA  AAATCTCTAG  TGTATCAGAA  GTA ATG AAA GAA TCT AAA CAG CCT              114
                                       Met Lys Glu Ser Lys Gln Pro
                                        1               5

GCC TCA CAA CTC CAA AAA CAA AAG GGA GAT ACT CCA GCT TCA GCA ACA                  162
Ala Ser Gln Leu Gln Lys Gln Lys Gly Asp Thr Pro Ala Ser Ala Thr
         10              15                  20

GCA CCT ACA GAA GCG GCT CAA ATT ATT TCT GCA GCA GGT GAT ACC CTG                  210
Ala Pro Thr Glu Ala Ala Gln Ile Ile Ser Ala Ala Gly Asp Thr Leu
```

|  |  |  |  |  |  |  |  |  |  |  |  |  |  |  |  |
|---|---|---|---|---|---|---|---|---|---|---|---|---|---|---|---|
|  |  | 25 |  |  |  |  | 30 |  |  |  |  | 35 |  |  |  |

```
        25                              30                              35
TCG  GTC  CCA  GCC  CCT  GCA  GTT  CAG  CCT  GAG  GAA  TCT  TTA  AAA  ACT  GAT    258
Ser  Val  Pro  Ala  Pro  Ala  Val  Gln  Pro  Glu  Glu  Ser  Leu  Lys  Thr  Asp
40             45                       50                            55

CAC  CCT  GAA  ATT  GGT  GAA  GGA  AAA  CCC  ACA  CCT  GCA  CTT  TCA  GAA  GCA    306
His  Pro  Glu  Ile  Gly  Glu  Gly  Lys  Pro  Thr  Pro  Ala  Leu  Ser  Glu  Ala
                         60                  65                  70

TCC  TCA  TCT  TCT  ATA  AGG  GAG  CGA  CCA  CCT  GAA  GAA  GTT  GCA  GCT  CGC    354
Ser  Ser  Ser  Ser  Ile  Arg  Glu  Arg  Pro  Pro  Glu  Glu  Val  Ala  Ala  Arg
               75                       80                       85

CTT  GCA  CAA  CAG  GAA  AAA  CAA  GAA  CAA  GTT  AAA  ATT  GAG  TCT  CTA  GCC    402
Leu  Ala  Gln  Gln  Glu  Lys  Gln  Glu  Gln  Val  Lys  Ile  Glu  Ser  Leu  Ala
               90                  95                       100

AAG  AGC  TTA  GAA  GAT  GCT  CTG  AGG  CAA  ACT  GCA  AGT  GTC  ACT  CTG  CAG    450
Lys  Ser  Leu  Glu  Asp  Ala  Leu  Arg  Gln  Thr  Ala  Ser  Val  Thr  Leu  Gln
     105                      110                      115

GCT  ATT  GCA  GCT  CAG  AAT  GCT  GCG  GTC  CAG  GCT  GTC  AAT  GCA  CAC  TCC    498
Ala  Ile  Ala  Ala  Gln  Asn  Ala  Ala  Val  Gln  Ala  Val  Asn  Ala  His  Ser
120                      125                      130                      135

AAC  ATA  TTG  AAA  GCC  GCC  ATG  GAC  AAT  TCT  GAG  ATT  GCA  GGC  GAG  AAG    546
Asn  Ile  Leu  Lys  Ala  Ala  Met  Asp  Asn  Ser  Glu  Ile  Ala  Gly  Glu  Lys
                         140                      145                      150

AAA  TCT  GCT  CAG  TGG  CGC  ACA  GTG  GAG  GGT  GCA  TTG  AAG  GAA  CGC  AGA    594
Lys  Ser  Ala  Gln  Trp  Arg  Thr  Val  Glu  Gly  Ala  Leu  Lys  Glu  Arg  Arg
               155                      160                      165

AAG  GCA  GTA  GAT  GAA  GCT  GCC  GAT  GCC  CTT  CTC  AAA  GCC  AAA  GAA  GAG    642
Lys  Ala  Val  Asp  Glu  Ala  Ala  Asp  Ala  Leu  Leu  Lys  Ala  Lys  Glu  Glu
               170                      175                      180

TTA  GAG  AAG  ATG  AAA  AGT  GTG  ATT  GAA  AAT  GCA  AAG  AAA  AAA  GAG  GTT    690
Leu  Glu  Lys  Met  Lys  Ser  Val  Ile  Glu  Asn  Ala  Lys  Lys  Lys  Glu  Val
     185                      190                      195

GCT  GGG  GCC  AAG  CCT  CAT  ATA  ACT  GCT  GCA  GAG  GGT  AAA  CTT  CAC  AAC    738
Ala  Gly  Ala  Lys  Pro  His  Ile  Thr  Ala  Ala  Glu  Gly  Lys  Leu  His  Asn
200                      205                      210                      215

ATG  ATA  GTT  GAT  CTG  GAT  AAT  GTG  GTC  AAA  AAG  GTC  CAA  GCA  GCT  CAG    786
Met  Ile  Val  Asp  Leu  Asp  Asn  Val  Val  Lys  Lys  Val  Gln  Ala  Ala  Gln
                         220                      225                      230

TCT  GAG  GCT  AAG  GTT  GTA  TCT  CAG  TAT  CAT  GAG  CTG  GTG  GTC  CAA  GCT    834
Ser  Glu  Ala  Lys  Val  Val  Ser  Gln  Tyr  His  Glu  Leu  Val  Val  Gln  Ala
               235                      240                      245

CGG  GAT  GAC  TTT  AAA  CGA  GAG  CTG  GAC  AGT  ATT  ACT  CCA  GAA  GTC  CTT    882
Arg  Asp  Asp  Phe  Lys  Arg  Glu  Leu  Asp  Ser  Ile  Thr  Pro  Glu  Val  Leu
               250                      255                      260

CCT  GGG  TGG  AAA  GGA  ATG  AGT  GTT  TCA  GAC  TTA  GCT  GAC  AAG  CTC  TCT    930
Pro  Gly  Trp  Lys  Gly  Met  Ser  Val  Ser  Asp  Leu  Ala  Asp  Lys  Leu  Ser
     265                      270                      275

ACT  GAT  GAT  CTG  AAC  TCC  CTC  ATT  GCT  CAT  GCA  CAT  CGT  CGT  ATT  GAT    978
Thr  Asp  Asp  Leu  Asn  Ser  Leu  Ile  Ala  His  Ala  His  Arg  Arg  Ile  Asp
280                      285                      290                      295

CAG  CTG  AAC  AGA  GAG  CTG  GCA  GAA  CAG  AAG  GCC  ACC  GAA  AAG  CAG  CAC    1026
Gln  Leu  Asn  Arg  Glu  Leu  Ala  Glu  Gln  Lys  Ala  Thr  Glu  Lys  Gln  His
                         300                      305                      310

ATC  ACG  TTA  GCC  TTG  GAG  AAA  CAA  AAG  CTG  GAA  GAA  AAG  CGG  GCA  TTT    1074
Ile  Thr  Leu  Ala  Leu  Glu  Lys  Gln  Lys  Leu  Glu  Glu  Lys  Arg  Ala  Phe
               315                      320                      325

GAC  TCT  GCA  GTA  GCA  AAA  GCA  TTA  GAA  CAT  CAC  AGA  AGT  GAA  ATA  CAG    1122
Asp  Ser  Ala  Val  Ala  Lys  Ala  Leu  Glu  His  His  Arg  Ser  Glu  Ile  Gln
          330                      335                      340

GCT  GAA  CAG  GAC  AGA  AAG  ATA  GAA  GAA  GTC  AGA  GAT  GCC  ATG  GAA  AAT    1170
Ala  Glu  Gln  Asp  Arg  Lys  Ile  Glu  Glu  Val  Arg  Asp  Ala  Met  Glu  Asn
```

-continued

```
              345                           350                           355
GAA  ATG  AGA  ACC  CCT  TCG  CCG  ACA  GCA  GCT  GCC  CAC  ACT  GAT  CAC  TTG    1218
Glu  Met  Arg  Thr  Pro  Ser  Pro  Thr  Ala  Ala  Ala  His  Thr  Asp  His  Leu
360                           365                      370                     375

CGA  GAT  GTC  CTT  AGG  GTA  CAA  GAA  CAG  GAA  TTG  AAG  TCT  GAA  TTT  GAG    1266
Arg  Asp  Val  Leu  Arg  Val  Gln  Glu  Gln  Glu  Leu  Lys  Ser  Glu  Phe  Glu
                    380                      385                          390

CAG  AAC  CTG  TCT  GAG  AAA  CTC  TCT  GAA  CAA  GAA  TTA  CAA  TTT  CGT  CGT    1314
Gln  Asn  Leu  Ser  Glu  Lys  Leu  Ser  Glu  Gln  Glu  Leu  Gln  Phe  Arg  Arg
               395                      400                     405

CTC  AGT  CAA  GAG  CAA  GTT  GAC  AAC  TTT  ACT  CTG  GAT  ATA  AAT  ACT  GCC    1362
Leu  Ser  Gln  Glu  Gln  Val  Asp  Asn  Phe  Thr  Leu  Asp  Ile  Asn  Thr  Ala
          410                      415                     420

TAT  GCC  AGA  CTC  AGA  GGA  ATC  GAA  CAG  GCT  GTT  CAG  AGC  CAT  GCA  GTT    1410
Tyr  Ala  Arg  Leu  Arg  Gly  Ile  Glu  Gln  Ala  Val  Gln  Ser  His  Ala  Val
     425                      430                     435

GCT  GAA  GAG  GAA  GCC  AGA  AAA  GCC  CAC  CAA  CTC  TGG  CTT  TCA  GTG  GAG    1458
Ala  Glu  Glu  Glu  Ala  Arg  Lys  Ala  His  Gln  Leu  Trp  Leu  Ser  Val  Glu
440                      445                     450                          455

GCA  TTA  AAG  TAC  AGC  ATG  AAG  ACC  TCA  TCT  GCA  GAA  ACA  CCT  ACT  ATC    1506
Ala  Leu  Lys  Tyr  Ser  Met  Lys  Thr  Ser  Ser  Ala  Glu  Thr  Pro  Thr  Ile
                    460                      465                         470

CCG  CTG  GGT  AGT  GCG  GTT  GAG  GCC  ATC  AAA  GCC  AAC  TGT  TCT  GAT  AAT    1554
Pro  Leu  Gly  Ser  Ala  Val  Glu  Ala  Ile  Lys  Ala  Asn  Cys  Ser  Asp  Asn
               475                      480                    485

GAA  TTC  ACC  CAA  GCT  TTA  ACC  GCA  GCT  ATC  CCT  CCA  GAG  TCC  CTG  ACC    1602
Glu  Phe  Thr  Gln  Ala  Leu  Thr  Ala  Ala  Ile  Pro  Pro  Glu  Ser  Leu  Thr
          490                      495                    500

CGT  GGG  GTG  TAC  AGT  GAA  GAG  ACC  CTT  AGA  GCC  CGT  TTC  TAT  GCT  GTT    1650
Arg  Gly  Val  Tyr  Ser  Glu  Glu  Thr  Leu  Arg  Ala  Arg  Phe  Tyr  Ala  Val
     505                      510                    515

CAA  AAA  CTG  GCC  CGA  AGG  GTA  GCA  ATG  ATT  GAT  GAA  ACC  AGA  AAT  AGC    1698
Gln  Lys  Leu  Ala  Arg  Arg  Val  Ala  Met  Ile  Asp  Glu  Thr  Arg  Asn  Ser
520                      525                     530                         535

TTG  TAC  CAG  TAC  TTC  CTC  TCC  TAC  CTA  CAG  TCC  CTG  CTC  CTA  TTC  CCA    1746
Leu  Tyr  Gln  Tyr  Phe  Leu  Ser  Tyr  Leu  Gln  Ser  Leu  Leu  Leu  Phe  Pro
                    540                      545                         550

CCT  CAG  CAA  CTG  AAG  CCG  CCC  CCA  GAG  CTC  TGC  CCT  GAG  GAT  ATA  AAC    1794
Pro  Gln  Gln  Leu  Lys  Pro  Pro  Pro  Glu  Leu  Cys  Pro  Glu  Asp  Ile  Asn
               555                      560                    565

ACA  TTT  AAA  TTA  CTG  TCA  TAT  GCT  TCC  TAT  TGC  ATT  GAG  CAT  GGT  GAT    1842
Thr  Phe  Lys  Leu  Leu  Ser  Tyr  Ala  Ser  Tyr  Cys  Ile  Glu  His  Gly  Asp
          570                      575                    580

CTG  GAG  CTA  GCA  GCA  AAG  TTT  GTC  AAT  CAG  CTG  AAG  GGG  GAA  TCC  AGA    1890
Leu  Glu  Leu  Ala  Ala  Lys  Phe  Val  Asn  Gln  Leu  Lys  Gly  Glu  Ser  Arg
     585                      590                    595

CGA  GTG  GCA  CAG  GAC  TGG  CTG  AAG  GAA  GCC  CGA  ATG  ACC  CTA  GAA  ACG    1938
Arg  Val  Ala  Gln  Asp  Trp  Leu  Lys  Glu  Ala  Arg  Met  Thr  Leu  Glu  Thr
600                      605                     610                         615

AAA  CAG  ATA  GTG  GAA  ATC  CTG  ACA  GCA  TAT  GCC  AGC  GCC  GTA  GGA  ATA    1986
Lys  Gln  Ile  Val  Glu  Ile  Leu  Thr  Ala  Tyr  Ala  Ser  Ala  Val  Gly  Ile
                    620                      625                         630

GGA  ACC  ACT  CAG  GTG  CAG  CCA  GAG  TGAGGTTTAG  GAAGATTTTC  ATAAAGTCAT        2040
Gly  Thr  Thr  Gln  Val  Gln  Pro  Glu
               635

ATTTCATGTC  AAAGGAAATC  AGCAGTGATA  GATGAAGGGT  TCGCAGCGAG  AGTCCCGGAC            2100

TTGTCTAGAA  ATGAGCAGGT  TTACAAGTAC  TGTTCTAAAT  GTTAACACCT  GTTGCATTTA            2160

TATTCTTTCC  ATTTGCTATC  ATGTCAGTGA  ACGCCAGGAG  TGCTTTCTTT  GCAACTTGTG            2220
```

```
TAACATTTTC TGTTTTTTCA GGTTTTACTG ATGAGGCTTG TGAGGCCAAT CAAAATAATG      2280

TTTGTGATCT CTACTACTGT TGATTTTGCC CTCGGAGCAA ACTGAATAAA GCAACAAGAT      2340

GAAAAAAAAA AAAAAAAAA                                                   2360
```

( 2 ) INFORMATION FOR SEQ ID NO:2:

( i ) SEQUENCE CHARACTERISTICS:
        ( A ) LENGTH: 639 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Lys  Glu  Ser  Lys  Gln  Pro  Ala  Ser  Gln  Leu  Gln  Lys  Gln  Lys  Gly
 1                   5                        10                       15

Asp  Thr  Pro  Ala  Ser  Ala  Thr  Ala  Pro  Thr  Glu  Ala  Ala  Gln  Ile  Ile
              20                        25                       30

Ser  Ala  Ala  Gly  Asp  Thr  Leu  Ser  Val  Pro  Ala  Pro  Ala  Val  Gln  Pro
                   35                        40                       45

Glu  Glu  Ser  Leu  Lys  Thr  Asp  His  Pro  Glu  Ile  Gly  Glu  Gly  Lys  Pro
     50                        55                        60

Thr  Pro  Ala  Leu  Ser  Glu  Ala  Ser  Ser  Ser  Ile  Arg  Glu  Arg  Pro
 65                       70                        75                       80

Pro  Glu  Glu  Val  Ala  Ala  Arg  Leu  Ala  Gln  Gln  Glu  Lys  Gln  Glu  Gln
                        85                        90                       95

Val  Lys  Ile  Glu  Ser  Leu  Ala  Lys  Ser  Leu  Glu  Asp  Ala  Leu  Arg  Gln
                    100                      105                      110

Thr  Ala  Ser  Val  Thr  Leu  Gln  Ala  Ile  Ala  Ala  Gln  Asn  Ala  Ala  Val
               115                      120                      125

Gln  Ala  Val  Asn  Ala  His  Ser  Asn  Ile  Leu  Lys  Ala  Ala  Met  Asp  Asn
 130                     135                      140

Ser  Glu  Ile  Ala  Gly  Glu  Lys  Lys  Ser  Ala  Gln  Trp  Arg  Thr  Val  Glu
 145                     150                      155                      160

Gly  Ala  Leu  Lys  Glu  Arg  Arg  Lys  Ala  Val  Asp  Glu  Ala  Ala  Asp  Ala
                    165                      170                      175

Leu  Leu  Lys  Ala  Lys  Glu  Glu  Leu  Glu  Lys  Met  Lys  Ser  Val  Ile  Glu
               180                      185                      190

Asn  Ala  Lys  Lys  Lys  Glu  Val  Ala  Gly  Ala  Lys  Pro  His  Ile  Thr  Ala
               195                      200                      205

Ala  Glu  Gly  Lys  Leu  His  Asn  Met  Ile  Val  Asp  Leu  Asp  Asn  Val  Val
     210                      215                      220

Lys  Lys  Val  Gln  Ala  Ala  Gln  Ser  Glu  Ala  Lys  Val  Val  Ser  Gln  Tyr
 225                     230                      235                      240

His  Glu  Leu  Val  Val  Gln  Ala  Arg  Asp  Asp  Phe  Lys  Arg  Glu  Leu  Asp
                    245                      250                      255

Ser  Ile  Thr  Pro  Glu  Val  Leu  Pro  Gly  Trp  Lys  Gly  Met  Ser  Val  Ser
               260                      265                      270

Asp  Leu  Ala  Asp  Lys  Leu  Ser  Thr  Asp  Asp  Leu  Asn  Ser  Leu  Ile  Ala
               275                      280                      285

His  Ala  His  Arg  Arg  Ile  Asp  Gln  Leu  Asn  Arg  Glu  Leu  Ala  Glu  Gln
     290                      295                      300

Lys  Ala  Thr  Glu  Lys  Gln  His  Ile  Thr  Leu  Ala  Leu  Glu  Lys  Gln  Lys
 305                     310                      315                      320

Leu  Glu  Glu  Lys  Arg  Ala  Phe  Asp  Ser  Ala  Val  Ala  Lys  Ala  Leu  Glu
                    325                      330                      335
```

| | | | | | | | | | | | | | | |
|---|---|---|---|---|---|---|---|---|---|---|---|---|---|---|
| His | His | Arg | Ser 340 | Glu | Ile | Gln | Ala | Glu 345 | Gln | Asp | Arg | Lys | Ile 350 | Glu | Glu |
| Val | Arg | Asp 355 | Ala | Met | Glu | Asn | Glu 360 | Met | Arg | Thr | Pro | Ser 365 | Pro | Thr | Ala |
| Ala | Ala 370 | His | Thr | Asp | His | Leu 375 | Arg | Asp | Val | Leu | Arg 380 | Val | Gln | Glu | Gln |
| Glu 385 | Leu | Lys | Ser | Glu | Phe 390 | Glu | Gln | Asn | Leu | Ser 395 | Glu | Lys | Leu | Ser | Glu 400 |
| Gln | Glu | Leu | Gln | Phe 405 | Arg | Arg | Leu | Ser | Gln 410 | Glu | Gln | Val | Asp | Asn 415 | Phe |
| Thr | Leu | Asp | Ile 420 | Asn | Thr | Ala | Tyr | Ala 425 | Arg | Leu | Arg | Gly | Ile 430 | Glu | Gln |
| Ala | Val | Gln 435 | Ser | His | Ala | Val | Ala 440 | Glu | Glu | Glu | Ala | Arg 445 | Lys | Ala | His |
| Gln | Leu 450 | Trp | Leu | Ser | Val | Glu 455 | Ala | Leu | Lys | Tyr | Ser 460 | Met | Lys | Thr | Ser |
| Ser 465 | Ala | Glu | Thr | Pro | Thr 470 | Ile | Pro | Leu | Gly | Ser 475 | Ala | Val | Glu | Ala | Ile 480 |
| Lys | Ala | Asn | Cys | Ser 485 | Asp | Asn | Glu | Phe | Thr 490 | Gln | Ala | Leu | Thr | Ala 495 | Ala |
| Ile | Pro | Pro | Glu 500 | Ser | Leu | Thr | Arg | Gly 505 | Val | Tyr | Ser | Glu | Glu 510 | Thr | Leu |
| Arg | Ala | Arg 515 | Phe | Tyr | Ala | Val | Gln 520 | Lys | Leu | Ala | Arg | Arg 525 | Val | Ala | Met |
| Ile | Asp 530 | Glu | Thr | Arg | Asn | Ser 535 | Leu | Tyr | Gln | Tyr | Phe 540 | Leu | Ser | Tyr | Leu |
| Gln 545 | Ser | Leu | Leu | Leu | Phe 550 | Pro | Pro | Gln | Gln | Leu 555 | Lys | Pro | Pro | Pro | Glu 560 |
| Leu | Cys | Pro | Glu | Asp 565 | Ile | Asn | Thr | Phe | Lys 570 | Leu | Leu | Ser | Tyr | Ala 575 | Ser |
| Tyr | Cys | Ile | Glu 580 | His | Gly | Asp | Leu | Glu 585 | Leu | Ala | Ala | Lys | Phe 590 | Val | Asn |
| Gln | Leu | Lys 595 | Gly | Glu | Ser | Arg | Arg 600 | Val | Ala | Gln | Asp | Trp 605 | Leu | Lys | Glu |
| Ala | Arg 610 | Met | Thr | Leu | Glu | Thr 615 | Lys | Gln | Ile | Val | Glu 620 | Ile | Leu | Thr | Ala |
| Tyr 625 | Ala | Ser | Ala | Val | Gly 630 | Ile | Gly | Thr | Thr | Gln 635 | Val | Gln | Pro | Glu | |

( 2 ) INFORMATION FOR SEQ ID NO:3:

( i ) SEQUENCE CHARACTERISTICS:
        ( A ) LENGTH: 6306 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..6306

( x ) PUBLICATION INFORMATION:
        ( A ) AUTHORS: COMPTON, DUANE A
                      SZILAK, ILYA
                      CLEVELAND, DON W
        ( B ) TITLE: PRIMARY STRUCTURE OF NUMA, AN INTRANUCLEAR
                PROTEIN THAT DEFINES A NOVEL PATHWAY FOR
                SEGREGATION OF PROTEINS AT MITOSIS (C) JOURNAL: J. Cell Biol.
(D) VOLUME: 116
(F) PAGES: 1395-1408
(G) DATE: 1992

(xi) SEQUENCE DESCRIPTION: SEQ ID NO:3:

```
ATG ACA CTC CAC GCC ACC CGG GGG GCT GCA CTC CTC TCT TGG GTG AAC       48
Met Thr Leu His Ala Thr Arg Gly Ala Ala Leu Leu Ser Trp Val Asn
 1               5                  10                  15

AGT CTA CAC GTG GCT GAC CCT GTG GAG GCT GTG CTG CAG CTC CAG GAC       96
Ser Leu His Val Ala Asp Pro Val Glu Ala Val Leu Gln Leu Gln Asp
             20                  25                  30

TGC AGC ATC TTC ATC AAG ATC ATT GAC AGA ATC CAT GGC ACT GAA GAG      144
Cys Ser Ile Phe Ile Lys Ile Ile Asp Arg Ile His Gly Thr Glu Glu
             35                  40                  45

GGA CAG CAA ATC TTG AAG CAG CCG GTG TCA GAG AGA CTG GAC TTT GTG      192
Gly Gln Gln Ile Leu Lys Gln Pro Val Ser Glu Arg Leu Asp Phe Val
 50                  55                  60

TGC AGT TTT CTG CAG AAA AAT CGA AAA CAT CCC TCT TCC CCA GAA TGC      240
Cys Ser Phe Leu Gln Lys Asn Arg Lys His Pro Ser Ser Pro Glu Cys
 65                  70                  75                  80

CTG GTA TCT GCA CAG AAG GTG CTA GAG GGA TCA GAG CTG GAA CTG GCG      288
Leu Val Ser Ala Gln Lys Val Leu Glu Gly Ser Glu Leu Glu Leu Ala
             85                  90                  95

AAG ATG ACC ATG CTG CTC TTA TAC CAC TCT ACC ATG AGC TCC AAA AGT      336
Lys Met Thr Met Leu Leu Leu Tyr His Ser Thr Met Ser Ser Lys Ser
            100                 105                 110

CCC AGG GAC TGG GAA CAG TTT GAA TAT AAA ATT CAG GCT GAG TTG GCT      384
Pro Arg Asp Trp Glu Gln Phe Glu Tyr Lys Ile Gln Ala Glu Leu Ala
            115                 120                 125

GTC ATT CTT AAA TTT GTG CTG GAC CAT GAG GAC GGG CTA AAC CTT AAT      432
Val Ile Leu Lys Phe Val Leu Asp His Glu Asp Gly Leu Asn Leu Asn
130                 135                 140

GAG GAC CTA GAG AAC TTC CTA CAG AAA GCT CCT GTG CCT TCT ACC TGT      480
Glu Asp Leu Glu Asn Phe Leu Gln Lys Ala Pro Val Pro Ser Thr Cys
145                 150                 155                 160

TCT AGC ACA TTC CCT GAA GAG CTC TCC CCA CCT AGC CAC CAG GCC AAG      528
Ser Ser Thr Phe Pro Glu Glu Leu Ser Pro Pro Ser His Gln Ala Lys
                165                 170                 175

AGG GAG ATT CGC TTC CTA GAG CTA CAG AAG GTT GCC TCC TCT TCC AGT      576
Arg Glu Ile Arg Phe Leu Glu Leu Gln Lys Val Ala Ser Ser Ser Ser
            180                 185                 190

GGG AAC AAC TTT CTC TCA GGT TCT CCA GCT TCT CCC ATG GGT GAT ATC      624
Gly Asn Asn Phe Leu Ser Gly Ser Pro Ala Ser Pro Met Gly Asp Ile
            195                 200                 205

CTG CAG ACC CCA CAG TTC CAG ATG AGA CGG CTG AAG AAG CAG CTT GCT      672
Leu Gln Thr Pro Gln Phe Gln Met Arg Arg Leu Lys Lys Gln Leu Ala
            210                 215                 220

GAT GAG AGA AGT AAT AGG GAT GAG CTG GAG CTG GAG CTA GCT GAG AAC      720
Asp Glu Arg Ser Asn Arg Asp Glu Leu Glu Leu Glu Leu Ala Glu Asn
225                 230                 235                 240

CGC AAG CTC CTC ACC GAG AAG GAT GCA CAG ATA GCC ATG ATG CAG CAG      768
Arg Lys Leu Leu Thr Glu Lys Asp Ala Gln Ile Ala Met Met Gln Gln
                245                 250                 255

CGC ATT GAC CGC CTA GCC CTG CTG AAT GAG AAG CAG GCG GCC AGC CCA      816
Arg Ile Asp Arg Leu Ala Leu Leu Asn Glu Lys Gln Ala Ala Ser Pro
            260                 265                 270

CTG GAG CCC AAG GAG CTT GAG GAG CTG CGT GAC AAG AAT GAG AGC CTT      864
Leu Glu Pro Lys Glu Leu Glu Glu Leu Arg Asp Lys Asn Glu Ser Leu
            275                 280                 285

ACC ATG CGG CTG CAT GAA ACC CTG AAG CAG TGC CAG GAC CTG AAG ACA      912
```

-continued

| | | | | | | | | | | | | | | | | |
|---|---|---|---|---|---|---|---|---|---|---|---|---|---|---|---|---|
| | Thr<br>290 | Met | Arg | Leu | His | Glu | Thr<br>295 | Leu | Lys | Gln | Cys | Gln<br>300 | Asp | Leu | Lys | Thr | |
| GAG<br>Glu<br>305 | AAG<br>Lys | AGC<br>Ser | CAG<br>Gln | ATG<br>Met | GAT<br>Asp<br>310 | CGC<br>Arg | AAA<br>Lys | ATC<br>Ile | AAC<br>Asn | CAG<br>Gln<br>315 | CTT<br>Leu | TCG<br>Ser | GAG<br>Glu | GAG<br>Glu | AAT<br>Asn<br>320 | 960 |
| GGA<br>Gly | GAC<br>Asp | CTT<br>Leu | TCC<br>Ser | TTT<br>Phe<br>325 | AAG<br>Lys | CTG<br>Leu | CGG<br>Arg | GAG<br>Glu | TTT<br>Phe<br>330 | GCC<br>Ala | AGT<br>Ser | CAT<br>His | CTG<br>Leu | CAG<br>Gln<br>335 | CAG<br>Gln | 1008 |
| CTA<br>Leu | CAG<br>Gln | GAT<br>Asp | GCC<br>Ala<br>340 | CTC<br>Leu | AAT<br>Asn | GAG<br>Glu | CTG<br>Leu | ACG<br>Thr<br>345 | GAG<br>Glu | GAG<br>Glu | CAC<br>His | AGC<br>Ser | AAG<br>Lys<br>350 | GCC<br>Ala | ACT<br>Thr | 1056 |
| CAG<br>Gln | GAG<br>Glu | TGG<br>Trp<br>355 | CTA<br>Leu | GAG<br>Glu | AAG<br>Lys | CAG<br>Gln | GCC<br>Ala<br>360 | CAG<br>Gln | CTG<br>Leu | GAG<br>Glu | AAG<br>Lys | GAG<br>Glu<br>365 | CTC<br>Leu | AGC<br>Ser | GCA<br>Ala | 1104 |
| GCC<br>Ala | CTG<br>Leu<br>370 | CAG<br>Gln | GAC<br>Asp | AAG<br>Lys | AAA<br>Lys | TGC<br>Cys<br>375 | CTT<br>Leu | GAA<br>Glu | GAG<br>Glu | AAG<br>Lys | AAC<br>Asn<br>380 | GAA<br>Glu | ATC<br>Ile | CTT<br>Leu | CAG<br>Gln | 1152 |
| GGA<br>Gly<br>385 | AAA<br>Lys | CTT<br>Leu | TCA<br>Ser | CAG<br>Gln | CTG<br>Leu<br>390 | GAA<br>Glu | GAA<br>Glu | CAC<br>His | TTG<br>Leu | TCC<br>Ser<br>395 | CAG<br>Gln | CTG<br>Leu | CAG<br>Gln | GAT<br>Asp | AAC<br>Asn<br>400 | 1200 |
| CCA<br>Pro | CCC<br>Pro | CAG<br>Gln | GAG<br>Glu | AAG<br>Lys<br>405 | GGC<br>Gly | GAG<br>Glu | GTG<br>Val | CTG<br>Leu | GGT<br>Gly<br>410 | GAT<br>Asp | GTC<br>Val | TTG<br>Leu | CAG<br>Gln | CTG<br>Leu<br>415 | GAA<br>Glu | 1248 |
| ACC<br>Thr | TTG<br>Leu | AAG<br>Lys | CAA<br>Gln<br>420 | GAG<br>Glu | GCA<br>Ala | GCC<br>Ala | ACT<br>Thr | CTT<br>Leu<br>425 | GCT<br>Ala | GCA<br>Ala | AAC<br>Asn | AAC<br>Asn | ACA<br>Thr<br>430 | CAG<br>Gln | CTC<br>Leu | 1296 |
| CAA<br>Gln | GCC<br>Ala | AGG<br>Arg<br>435 | GTA<br>Val | GAG<br>Glu | ATG<br>Met | CTG<br>Leu | GAG<br>Glu<br>440 | ACT<br>Thr | GAG<br>Glu | CGA<br>Arg | GGC<br>Gly | CAG<br>Gln<br>445 | CAG<br>Gln | GAA<br>Glu | GCC<br>Ala | 1344 |
| AAG<br>Lys | CTG<br>Leu<br>450 | CTT<br>Leu | GCT<br>Ala | GAG<br>Glu | CGG<br>Arg | GGC<br>Gly<br>455 | CAC<br>His | TTC<br>Phe | GAA<br>Glu | GAA<br>Glu | GAA<br>Glu<br>460 | AAG<br>Lys | CAG<br>Gln | CAG<br>Gln | CTG<br>Leu | 1392 |
| TCT<br>Ser<br>465 | AGC<br>Ser | CTG<br>Leu | ATC<br>Ile | ACT<br>Thr | GAC<br>Asp<br>470 | CTG<br>Leu | CAG<br>Gln | AGC<br>Ser | TCC<br>Ser | ATC<br>Ile<br>475 | TCC<br>Ser | AAC<br>Asn | CTC<br>Leu | AGC<br>Ser | CAG<br>Gln<br>480 | 1440 |
| GCC<br>Ala | AAG<br>Lys | GAA<br>Glu | GAG<br>Glu | CTG<br>Leu<br>485 | GAG<br>Glu | CAG<br>Gln | GCC<br>Ala | TCC<br>Ser | CAG<br>Gln<br>490 | GCT<br>Ala | CAT<br>His | GGG<br>Gly | GCC<br>Ala | CGG<br>Arg<br>495 | TTG<br>Leu | 1488 |
| ACT<br>Thr | GCC<br>Ala | CAG<br>Gln | GTG<br>Val<br>500 | GCC<br>Ala | TCT<br>Ser | CTG<br>Leu | ACC<br>Thr | TCT<br>Ser<br>505 | GAG<br>Glu | CTC<br>Leu | ACC<br>Thr | ACA<br>Thr | CTC<br>Leu<br>510 | AAT<br>Asn | GCC<br>Ala | 1536 |
| ACC<br>Thr | ATC<br>Ile | CAG<br>Gln<br>515 | CAA<br>Gln | CAG<br>Gln | GAT<br>Asp | CAA<br>Gln | GAA<br>Glu<br>520 | CTG<br>Leu | GCT<br>Ala | GGC<br>Gly | CTG<br>Leu | AAG<br>Lys<br>525 | CAG<br>Gln | CAG<br>Gln | GCC<br>Ala | 1584 |
| AAA<br>Lys | GAG<br>Glu<br>530 | AAG<br>Lys | CAG<br>Gln | GCC<br>Ala | CAG<br>Gln | CTA<br>Leu<br>535 | GCA<br>Ala | CAG<br>Gln | ACC<br>Thr | CTC<br>Leu | CAA<br>Gln<br>540 | CAG<br>Gln | CAA<br>Gln | GAA<br>Glu | CAG<br>Gln | 1632 |
| GCC<br>Ala<br>545 | TCC<br>Ser | CAG<br>Gln | GGC<br>Gly | CTC<br>Leu | CGC<br>Arg<br>550 | CAC<br>His | CAG<br>Gln | GTG<br>Val | GAG<br>Glu | CAG<br>Gln<br>555 | CTA<br>Leu | AGC<br>Ser | AGT<br>Ser | AGC<br>Ser | CTG<br>Leu<br>560 | 1680 |
| AAG<br>Lys | CAG<br>Gln | AAG<br>Lys | GAG<br>Glu | CAG<br>Gln<br>565 | CAG<br>Gln | TTG<br>Leu | AAG<br>Lys | GAG<br>Glu | GTA<br>Val<br>570 | GCG<br>Ala | GAG<br>Glu | AAG<br>Lys | CAG<br>Gln | GAG<br>Glu<br>575 | GCA<br>Ala | 1728 |
| ACT<br>Thr | AGG<br>Arg | CAG<br>Gln | GAC<br>Asp<br>580 | CAT<br>His | GCC<br>Ala | CAG<br>Gln | CAA<br>Gln | CTG<br>Leu<br>585 | GCC<br>Ala | ACT<br>Thr | GCT<br>Ala | GCA<br>Ala | GAG<br>Glu<br>590 | GAG<br>Glu | CGA<br>Arg | 1776 |
| GAG<br>Glu | GCC<br>Ala | TCC<br>Ser<br>595 | TTA<br>Leu | AGG<br>Arg | GAG<br>Glu | CGG<br>Arg | GAT<br>Asp<br>600 | GCG<br>Ala | GCT<br>Ala | CTC<br>Leu | AAG<br>Lys | CAG<br>Gln<br>605 | CTG<br>Leu | GAG<br>Glu | GCA<br>Ala | 1824 |
| CTG<br>Leu | GAG<br>Glu | AAG<br>Lys | GAG<br>Glu | AAG<br>Lys | GCT<br>Ala | GCC<br>Ala | AAG<br>Lys | CTG<br>Leu | GAG<br>Glu | ATT<br>Ile | CTG<br>Leu | CAG<br>Gln | CAG<br>Gln | CAA<br>Gln | CTT<br>Leu | 1872 |

```
            Leu   Glu   Lys   Glu   Lys   Ala   Ala   Lys   Leu   Glu   Ile   Leu   Gln   Gln   Gln   Leu
                  610               615                           620

CAG  GTG  GCT  AAT  GAA  GCC  CGG  GAC  AGT  GCC  CAG  ACC  TCA  GTG  ACA  CAG      1920
Gln  Val  Ala  Asn  Glu  Ala  Arg  Asp  Ser  Ala  Gln  Thr  Ser  Val  Thr  Gln
625            630                      635                           640

GCC  CAG  CGG  GAG  AAG  GCA  GAG  CTG  AGC  CGG  AAG  GTG  GAG  GAA  CTC  CAG      1968
Ala  Gln  Arg  Glu  Lys  Ala  Glu  Leu  Ser  Arg  Lys  Val  Glu  Glu  Leu  Gln
               645                      650                           655

GCC  TGT  GTT  GAG  ACA  GCC  CGC  CAG  GAA  CAG  CAT  GAG  GCC  CAG  GCC  CAG      2016
Ala  Cys  Val  Glu  Thr  Ala  Arg  Gln  Glu  Gln  His  Glu  Ala  Gln  Ala  Gln
               660                      665                           670

GTT  GCA  GAG  CTA  GAG  TTG  CAG  CTG  CGG  TCT  GAG  CAG  CAA  AAA  GCA  ACT      2064
Val  Ala  Glu  Leu  Glu  Leu  Gln  Leu  Arg  Ser  Glu  Gln  Gln  Lys  Ala  Thr
               675                      680                           685

GAG  AAA  GAA  AGG  GTG  GCC  CAG  GAG  AAG  GAC  CAG  CTC  CAG  GAG  CAG  CTC      2112
Glu  Lys  Glu  Arg  Val  Ala  Gln  Glu  Lys  Asp  Gln  Leu  Gln  Glu  Gln  Leu
     690                 695                      700

CAG  GCC  CTC  AAA  GAG  TCC  TTG  AAG  GTC  ACC  AAG  GGC  AGC  CTT  GAA  GAG      2160
Gln  Ala  Leu  Lys  Glu  Ser  Leu  Lys  Val  Thr  Lys  Gly  Ser  Leu  Glu  Glu
705                 710                      715                           720

GAG  AAG  CGC  AGG  GCT  GCA  GAT  GCC  CTG  GAA  GAG  CAG  CAG  CGT  TGT  ATC      2208
Glu  Lys  Arg  Arg  Ala  Ala  Asp  Ala  Leu  Glu  Glu  Gln  Gln  Arg  Cys  Ile
                    725                      730                           735

TCT  GAG  CTG  AAG  GCA  GAG  ACC  CGA  AGC  CTG  GTG  GAG  CAG  CAT  AAG  CGG      2256
Ser  Glu  Leu  Lys  Ala  Glu  Thr  Arg  Ser  Leu  Val  Glu  Gln  His  Lys  Arg
               740                      745                           750

GAA  CGA  AAG  GAG  CTG  GAA  GAA  GAG  AGG  GCT  GGG  CGC  AAG  GGG  CTG  GAG      2304
Glu  Arg  Lys  Glu  Leu  Glu  Glu  Glu  Arg  Ala  Gly  Arg  Lys  Gly  Leu  Glu
          755                      760                      765

GCT  CGA  TTA  CTG  CAG  CTT  GGG  GAG  GCC  CAT  CAG  GCT  GAG  ACT  GAA  GTC      2352
Ala  Arg  Leu  Leu  Gln  Leu  Gly  Glu  Ala  His  Gln  Ala  Glu  Thr  Glu  Val
770                      775                      780

CTG  CGG  CGG  GAG  CTG  GCA  GAG  GCC  ATG  GCT  GCC  CAG  CAC  ACA  GCT  GAG      2400
Leu  Arg  Arg  Glu  Leu  Ala  Glu  Ala  Met  Ala  Ala  Gln  His  Thr  Ala  Glu
785                      790                      795                      800

AGT  GAG  TGT  GAG  CAG  CTC  GTC  AAA  GAA  GTA  GCT  GCC  TGG  CGT  GAC  GGG      2448
Ser  Glu  Cys  Glu  Gln  Leu  Val  Lys  Glu  Val  Ala  Ala  Trp  Arg  Asp  Gly
                    805                      810                           815

TAT  GAG  GAT  AGC  CAG  CAA  GAG  GAG  GCA  CAG  TAT  GGC  GCC  ATG  TTC  CAG      2496
Tyr  Glu  Asp  Ser  Gln  Gln  Glu  Glu  Ala  Gln  Tyr  Gly  Ala  Met  Phe  Gln
               820                      825                           830

GAA  CAG  CTG  ATG  ACT  TTG  AAG  GAG  GAA  TGT  GAG  AAG  GCC  CGC  CAG  GAG      2544
Glu  Gln  Leu  Met  Thr  Leu  Lys  Glu  Glu  Cys  Glu  Lys  Ala  Arg  Gln  Glu
          835                      840                      845

CTG  CAG  GAG  GCA  AAG  GAG  AAG  GTG  GCA  GGC  ATA  GAA  TCC  CAC  AGC  GAG      2592
Leu  Gln  Glu  Ala  Lys  Glu  Lys  Val  Ala  Gly  Ile  Glu  Ser  His  Ser  Glu
     850                 855                      860

CTC  CAG  ATA  AGC  CGG  CAG  CAG  AAC  AAA  CTA  GCT  GAG  CTC  CAT  GCC  AAC      2640
Leu  Gln  Ile  Ser  Arg  Gln  Gln  Asn  Lys  Leu  Ala  Glu  Leu  His  Ala  Asn
865                      870                      875                      880

CTG  GCC  AGA  GCA  CTC  CAG  CAG  GTC  CAA  GAG  AAG  GAA  GTC  AGG  GCC  CAG      2688
Leu  Ala  Arg  Ala  Leu  Gln  Gln  Val  Gln  Glu  Lys  Glu  Val  Arg  Ala  Gln
                    885                      890                           895

AAG  CTT  GCA  GAT  GAC  CTC  TCC  ACT  CTG  CAG  GAA  AAG  ATG  GCT  GCC  ACC      2736
Lys  Leu  Ala  Asp  Asp  Leu  Ser  Thr  Leu  Gln  Glu  Lys  Met  Ala  Ala  Thr
               900                      905                           910

AGC  AAA  GAG  GTG  GCC  CGC  TTG  GAG  ACC  TTG  GTC  CGC  AAG  GCA  GGT  GAG      2784
Ser  Lys  Glu  Val  Ala  Arg  Leu  Glu  Thr  Leu  Val  Arg  Lys  Ala  Gly  Glu
          915                      920                      925

CAG  CAG  GAA  ACA  GCC  TCC  CGG  GAG  TTA  GTC  AAG  GAG  CCT  GCG  AGG  GCA      2832
```

```
            Gln Gln Glu Thr Ala Ser Arg Glu Leu Val Lys Glu Pro Ala Arg Ala
                930             935                 940

GGA GAC AGA CAG CCC GAG TGG CTG GAA GAG CAA CAG GGA CGC CAG TTC            2880
Gly Asp Arg Gln Pro Glu Trp Leu Glu Glu Gln Gln Gly Arg Gln Phe
945             950                 955                 960

TGC AGC ACA CAG GCA GCG CTG CAG GCT ATG GAG CGG GAG GCA GAG CAG            2928
Cys Ser Thr Gln Ala Ala Leu Gln Ala Met Glu Arg Glu Ala Glu Gln
                965                 970                 975

ATG GGC AAT GAG CTG GAA CGG CTG CGG GCC GCG CTG ATG GAG AGC CAG            2976
Met Gly Asn Glu Leu Glu Arg Leu Arg Ala Ala Leu Met Glu Ser Gln
                980                 985                 990

GGG CAG CAG CAG GAG GAG CGT GGG CAG CAG GAA AGG GAG GTG GCG CGG            3024
Gly Gln Gln Gln Glu Glu Arg Gly Gln Gln Glu Arg Glu Val Ala Arg
995                 1000                1005

CTG ACC CAG GAG CGG GGC CGT GCC CAG GCT GAC CTT GCC CTG GAG AAG            3072
Leu Thr Gln Glu Arg Gly Arg Ala Gln Ala Asp Leu Ala Leu Glu Lys
1010                1015                1020

GCG GCC AGA GCA GAG CTT GAG ATG CGG CTG CAG AAC GCC CTC AAC GAG            3120
Ala Ala Arg Ala Glu Leu Glu Met Arg Leu Gln Asn Ala Leu Asn Glu
1025                1030                1035                1040

CAG CGT GTG GAG TTC GCT ACC CTG CAA GAG GCA CTG GCT CAT GCC CTG            3168
Gln Arg Val Glu Phe Ala Thr Leu Gln Glu Ala Leu Ala His Ala Leu
                1045                1050                1055

ACG GAA AAG GAA GGC AAG GAC CAG GAG TTG GCC AAG CTT CGT GGT CTG            3216
Thr Glu Lys Glu Gly Lys Asp Gln Glu Leu Ala Lys Leu Arg Gly Leu
                1060                1065                1070

GAG GCA GCC CAG ATA AAA GAG CTG GAG GAA CTT CGG CAA ACC GTG AAG            3264
Glu Ala Ala Gln Ile Lys Glu Leu Glu Glu Leu Arg Gln Thr Val Lys
                1075                1080                1085

CAA CTG AAG GAA CAG CTG GCT AAG AAA GAA AAG GAG CAC GCA TCT GGC            3312
Gln Leu Lys Glu Gln Leu Ala Lys Lys Glu Lys Glu His Ala Ser Gly
    1090                1095                1100

TCA GGA GCC CAA TCT GAG GCT GCT GGC AGG ACA GAG CCA ACA GGC CCC            3360
Ser Gly Ala Gln Ser Glu Ala Ala Gly Arg Thr Glu Pro Thr Gly Pro
1105                1110                1115                1120

AAG CTG GAA GCA CTG CGG GCA GAG GTG AGC AAG CTG GAA CAG CAA TGC            3408
Lys Leu Glu Ala Leu Arg Ala Glu Val Ser Lys Leu Glu Gln Gln Cys
                1125                1130                1135

CAG AAG CAG CAG GAG CAG GCT GAC AGC CTG GAA CGC AGC CTC GAG GCT            3456
Gln Lys Gln Gln Glu Gln Ala Asp Ser Leu Glu Arg Ser Leu Glu Ala
                1140                1145                1150

GAG CGG GCC TCC CGG GCT GAG CGG GAC AGT GCT CTG GAG ACT CTG CAG            3504
Glu Arg Ala Ser Arg Ala Glu Arg Asp Ser Ala Leu Glu Thr Leu Gln
                1155                1160                1165

GGC CAG TTA GAG GAG AAG GCC CAG GAG CTA GGG CAC AGT CAG AGT GCC            3552
Gly Gln Leu Glu Glu Lys Ala Gln Glu Leu Gly His Ser Gln Ser Ala
    1170                1175                1180

TTA GCC TCG GCC CAA CGG GAG TTG GCT GCC TTC CGC ACC AAG GTA CAA            3600
Leu Ala Ser Ala Gln Arg Glu Leu Ala Ala Phe Arg Thr Lys Val Gln
1185                1190                1195                1200

GAC CAC AGC AAG GCT GAA GAT GAG TGG AAG GCC CAG GTG GCC CGG GGC            3648
Asp His Ser Lys Ala Glu Asp Glu Trp Lys Ala Gln Val Ala Arg Gly
                1205                1210                1215

CGG CAA GAG GCT GAG AGG AAA AAT AGC CTC ATC AGC AGC TTG GAG GAG            3696
Arg Gln Glu Ala Glu Arg Lys Asn Ser Leu Ile Ser Ser Leu Glu Glu
                1220                1225                1230

GAG GTG TCC ATC CTG AAT CGC CAG GTC CTG GAG AAG GAG GGG GAG AGC            3744
Glu Val Ser Ile Leu Asn Arg Gln Val Leu Glu Lys Glu Gly Glu Ser
                1235                1240                1245

AAG GAG TTG AAG CGG CTG GTG ATG GCC GAG TCA GAG AAG AGC CAG AAG            3792
```

```
Lys Glu Leu Lys Arg Leu Val Met Ala Glu Ser Glu Lys Ser Gln Lys
    1250                1255                1260

CTG GAG GAG AGC TGC GCC TGC TGC AGG CAG AGA CAG CCA GCA ACA GTG          3840
Leu Glu Glu Ser Cys Ala Cys Cys Arg Gln Arg Gln Pro Ala Thr Val
1265            1270                1275                1280

CCA GAG CTG CAG AAC GCA GCT CTG CTC TGC GGG AGG AGG TGC AGA GCC          3888
Pro Glu Leu Gln Asn Ala Ala Leu Leu Cys Gly Arg Arg Cys Arg Ala
                1285                1290                1295

TCC GGG AGG GAG GCT GAG AAA CAG CGG GTG GCT TCA GAG AAC CTG CGG          3936
Ser Gly Arg Glu Ala Glu Lys Gln Arg Val Ala Ser Glu Asn Leu Arg
            1300                1305                1310

CAG GAG CTG ACC TCA CAG GCT GAG CGT GCG GAG GAG CTG GGC CAA GAA          3984
Gln Glu Leu Thr Ser Gln Ala Glu Arg Ala Glu Glu Leu Gly Gln Glu
        1315                1320                1325

TTG AAG GCG TGG CAG GAG AAG TTC TTC CAG AAA GAG CAG GCC CTC TCC          4032
Leu Lys Ala Trp Gln Glu Lys Phe Phe Gln Lys Glu Gln Ala Leu Ser
    1330                1335                1340

ACC CTG CAG CTC GAG CAC ACC AGC ACA CAG GCC CTG GTG AGT GAG CTG          4080
Thr Leu Gln Leu Glu His Thr Ser Thr Gln Ala Leu Val Ser Glu Leu
1345                1350                1355                1360

CTG CCA GCT AAG CAC CTC TGC CAG CAG CTG CAG GCC GAG CAG GCC GCT          4128
Leu Pro Ala Lys His Leu Cys Gln Gln Leu Gln Ala Glu Gln Ala Ala
                1365                1370                1375

GCC GAG AAA CGC CAC CGT GAG GAG CTG GAG CAG AGC AAG CAG GCC GCT          4176
Ala Glu Lys Arg His Arg Glu Glu Leu Glu Gln Ser Lys Gln Ala Ala
            1380                1385                1390

GGG GGA CTG CGG GCA GAG CTG CTG CGG GCC CAG CGG GAG CTT GGG GAG          4224
Gly Gly Leu Arg Ala Glu Leu Leu Arg Ala Gln Arg Glu Leu Gly Glu
        1395                1400                1405

CTG ATT CCT CTG CGG CAG AAG GTG GCA GAG CAG GAG CGA ACA GCT CAG          4272
Leu Ile Pro Leu Arg Gln Lys Val Ala Glu Gln Glu Arg Thr Ala Gln
    1410                1415                1420

CAG CTG CGG GCA GAG AAG GCC AGC TAT GCA GAG CAG CTG AGC ATG CTG          4320
Gln Leu Arg Ala Glu Lys Ala Ser Tyr Ala Glu Gln Leu Ser Met Leu
1425                1430                1435                1440

AAG AAG GCG CAT GGC CTG CTG GCA GAG GAG AAC CGG GGG CTG GGT GAG          4368
Lys Lys Ala His Gly Leu Leu Ala Glu Glu Asn Arg Gly Leu Gly Glu
                1445                1450                1455

CGG GCC AAC CTT GGC CGG CAG TTT CTG GAA GTG GAG TTG GAC CAG GCC          4416
Arg Ala Asn Leu Gly Arg Gln Phe Leu Glu Val Glu Leu Asp Gln Ala
            1460                1465                1470

CGG GAA AAG TAT GTC CAA GAG TTG GCA GCC GTA CGT GCT GAT GCT GAG          4464
Arg Glu Lys Tyr Val Gln Glu Leu Ala Ala Val Arg Ala Asp Ala Glu
        1475                1480                1485

ACC CGT CTG GCT GAG GTG CAG CGA GAA GCA CAG AGC ACT GCC CGG GAG          4512
Thr Arg Leu Ala Glu Val Gln Arg Glu Ala Gln Ser Thr Ala Arg Glu
    1490                1495                1500

CTG GAG GTG ATG ACT GCC AAG TAT GAG GGT GCC AAG GTC AAG GTC CTG          4560
Leu Glu Val Met Thr Ala Lys Tyr Glu Gly Ala Lys Val Lys Val Leu
1505                1510                1515                1520

GAG GAG AGG CAG CGG TTC CAG GAA GAG AGG CAG AAA CTC ACT GCC CAG          4608
Glu Glu Arg Gln Arg Phe Gln Glu Glu Arg Gln Lys Leu Thr Ala Gln
                1525                1530                1535

GTG GAA GAA CTG AGT AAG AAA CTG GCT GAC TCT GAC CAA GCC AGC AAG          4656
Val Glu Glu Leu Ser Lys Lys Leu Ala Asp Ser Asp Gln Ala Ser Lys
            1540                1545                1550

GTG CAG CAG CAG AAG CTG AAG GCT GTC CAG GCT CAG GGA GGC GAG AGC          4704
Val Gln Gln Gln Lys Leu Lys Ala Val Gln Ala Gln Gly Gly Glu Ser
        1555                1560                1565

CAG CAG GAG GCC CAG CGC TTC CAG GCC CAG CTG AAT GAA CTG CAA GCC          4752
```

```
                                                      -continued

Gln  Gln  Glu  Ala  Gln  Arg  Phe  Gln  Ala  Gln  Leu  Asn  Glu  Leu  Gln  Ala
     1570                     1575                    1580

CAG  TTG  AGC  CAG  AAG  GAG  CAG  GCA  GCT  GAG  CAC  TAT  AAG  CTG  CAG  ATG              4800
Gln  Leu  Ser  Gln  Lys  Glu  Gln  Ala  Ala  Glu  His  Tyr  Lys  Leu  Gln  Met
1585                     1590                    1595                     1600

GAG  AAA  GCC  AAA  ACA  CAT  TAT  GAT  GCC  AAG  AAG  CAG  CAG  AAC  CAA  GAG              4848
Glu  Lys  Ala  Lys  Thr  His  Tyr  Asp  Ala  Lys  Lys  Gln  Gln  Asn  Gln  Glu
                    1605                     1610                     1615

CTG  CAG  GAG  CAG  CTG  CGG  AGC  CTG  GAG  CAG  CTG  CAG  AAG  GAA  AAC  AAA              4896
Leu  Gln  Glu  Gln  Leu  Arg  Ser  Leu  Glu  Gln  Leu  Gln  Lys  Glu  Asn  Lys
               1620                     1625                     1630

GAG  CTG  CGA  GCT  GAA  GCT  GAA  CGG  CTG  GGC  CAT  GAG  CTA  CAG  CAG  GCT              4944
Glu  Leu  Arg  Ala  Glu  Ala  Glu  Arg  Leu  Gly  His  Glu  Leu  Gln  Gln  Ala
               1635                     1640                     1645

GGG  CTG  AAG  ACC  AAG  GAG  GCT  GAA  CAG  ACC  TGC  CGC  CAC  CTT  ACT  GCC              4992
Gly  Leu  Lys  Thr  Lys  Glu  Ala  Glu  Gln  Thr  Cys  Arg  His  Leu  Thr  Ala
1650                     1655                     1660

CAG  GTG  CGC  AGC  CTG  GAG  GCA  CAG  GTT  GCC  CAT  GCA  GAC  CAG  CAG  CTT              5040
Gln  Val  Arg  Ser  Leu  Glu  Ala  Gln  Val  Ala  His  Ala  Asp  Gln  Gln  Leu
1665                     1670                     1675                     1680

CGA  GAC  CTG  GGC  AAA  TTC  CAG  GTG  GCA  ACT  GAT  GCT  TTA  AAG  AGC  CGT              5088
Arg  Asp  Leu  Gly  Lys  Phe  Gln  Val  Ala  Thr  Asp  Ala  Leu  Lys  Ser  Arg
                    1685                     1690                     1695

GAG  CCC  CAG  GCT  AAG  CCC  CAG  CTG  GAC  TTG  AGT  ATT  GAC  AGC  CTG  GAT              5136
Glu  Pro  Gln  Ala  Lys  Pro  Gln  Leu  Asp  Leu  Ser  Ile  Asp  Ser  Leu  Asp
               1700                     1705                     1710

CTG  AGC  TGC  GAG  GAG  GGG  ACC  CCA  CTC  AGT  ATC  ACC  AGC  AAG  CTG  CCT              5184
Leu  Ser  Cys  Glu  Glu  Gly  Thr  Pro  Leu  Ser  Ile  Thr  Ser  Lys  Leu  Pro
               1715                     1720                     1725

CGT  ACC  CAG  CCA  GAC  GGC  ACC  AGC  GTC  CCT  GGA  GAA  CCA  GCC  TCA  CCT              5232
Arg  Thr  Gln  Pro  Asp  Gly  Thr  Ser  Val  Pro  Gly  Glu  Pro  Ala  Ser  Pro
1730                     1735                     1740

ATC  TCC  CAG  CGC  CTG  CCC  CCC  AAG  GTA  GAA  TCC  CTG  GAG  AGT  CTC  TAC              5280
Ile  Ser  Gln  Arg  Leu  Pro  Pro  Lys  Val  Glu  Ser  Leu  Glu  Ser  Leu  Tyr
1745                     1750                     1755                     1760

TTC  ACT  CCC  ATC  CCT  GCT  CGG  AGT  CAG  GCC  CCC  CTG  GAG  AGC  AGC  CTG              5328
Phe  Thr  Pro  Ile  Pro  Ala  Arg  Ser  Gln  Ala  Pro  Leu  Glu  Ser  Ser  Leu
                    1765                     1770                     1775

GAC  TCC  CTG  GGA  GAC  GTC  TTC  CTG  GAC  TCG  GGT  CGT  AAG  ACC  CGC  TCC              5376
Asp  Ser  Leu  Gly  Asp  Val  Phe  Leu  Asp  Ser  Gly  Arg  Lys  Thr  Arg  Ser
               1780                     1785                     1790

GCT  CGT  CGG  CGC  ACC  ACG  CAG  ATC  ATC  AAC  ATC  ACC  ATG  ACC  AAG  AAG              5424
Ala  Arg  Arg  Arg  Thr  Thr  Gln  Ile  Ile  Asn  Ile  Thr  Met  Thr  Lys  Lys
                    1795                     1800                     1805

CTA  GAT  GTG  GAA  GAG  CCA  GAC  AGC  GCC  AAC  TCA  TCG  TTC  TAC  AGC  ACG              5472
Leu  Asp  Val  Glu  Glu  Pro  Asp  Ser  Ala  Asn  Ser  Ser  Phe  Tyr  Ser  Thr
     1810                     1815                     1820

CGG  TCT  GCT  CCT  GCT  TCC  CAG  GCT  AGC  CTG  CGA  GCC  ACC  TCC  TCT  ACT              5520
Arg  Ser  Ala  Pro  Ala  Ser  Gln  Ala  Ser  Leu  Arg  Ala  Thr  Ser  Ser  Thr
1825                     1830                     1835                     1840

CAG  TCT  CTA  GCT  CGC  CTG  GGT  TCT  CCC  GAT  TAT  GGC  AAC  TCA  GCC  CTG              5568
Gln  Ser  Leu  Ala  Arg  Leu  Gly  Ser  Pro  Asp  Tyr  Gly  Asn  Ser  Ala  Leu
                    1845                     1850                     1855

CTC  AGC  TTG  CCT  GGC  TAC  CGC  CCC  ACC  ACT  CGC  AGT  CTG  CTC  CGT  CGT              5616
Leu  Ser  Leu  Pro  Gly  Tyr  Arg  Pro  Thr  Thr  Arg  Ser  Ser  Ala  Arg  Arg
               1860                     1865                     1870

TCC  CAG  GCC  GGG  GTG  TCC  AGT  GGG  GCC  CCT  CCA  GGA  AGG  AAC  AGC  TTC              5664
Ser  Gln  Ala  Gly  Val  Ser  Ser  Gly  Ala  Pro  Pro  Gly  Arg  Asn  Ser  Phe
               1875                     1880                     1885

TAC  ATG  GGC  ACT  TGC  CAG  GAT  GAG  CCT  GAG  CAG  CTG  GAT  GAC  TGG  AAC              5712
```

```
Tyr  Met  Gly  Thr  Cys  Gln  Asp  Glu  Pro  Glu  Gln  Leu  Asp  Asp  Trp  Asn
     1890                     1895                          1900

CGC  ATT  GCA  GAG  CTG  CAG  CAG  CGC  AAT  CGA  GTG  TGC  CCC  CCA  CAT  CTG      5760
Arg  Ile  Ala  Glu  Leu  Gln  Gln  Arg  Asn  Arg  Val  Cys  Pro  Pro  His  Leu
1905                     1910                     1915                     1920

AAG  ACC  TGC  TAT  CCC  CTG  GAG  TCC  AGG  CCT  TCC  CTG  AGC  CTG  GGC  ACC      5808
Lys  Thr  Cys  Tyr  Pro  Leu  Glu  Ser  Arg  Pro  Ser  Leu  Ser  Leu  Gly  Thr
                    1925                     1930                     1935

ATC  ACA  GAT  GAG  GAG  ATG  AAA  ACT  GGA  GAC  CCC  CAA  GAG  ACC  CTG  CGC      5856
Ile  Thr  Asp  Glu  Glu  Met  Lys  Thr  Gly  Asp  Pro  Gln  Glu  Thr  Leu  Arg
                    1940                     1945                     1950

CGA  GCC  AGC  ATG  CAG  CCA  ATC  CAG  ATA  GCC  GAG  GGC  ACT  GGC  ATC  ACC      5904
Arg  Ala  Ser  Met  Gln  Pro  Ile  Gln  Ile  Ala  Glu  Gly  Thr  Gly  Ile  Thr
               1955                     1960                     1965

ACC  CGG  CAG  CAG  CGC  AAA  CGG  GTC  TCC  CTA  GAG  CCC  CAC  CAG  GGC  CCT      5952
Thr  Arg  Gln  Gln  Arg  Lys  Arg  Val  Ser  Leu  Glu  Pro  His  Gln  Gly  Pro
          1970                     1975                     1980

GGA  ACT  CCT  GAG  TCT  AAG  AAG  GCC  ACC  AGC  TGT  TTC  CCA  CGC  CCC  ATG      6000
Gly  Thr  Pro  Glu  Ser  Lys  Lys  Ala  Thr  Ser  Cys  Phe  Pro  Arg  Pro  Met
1985                     1990                     1995                     2000

ACT  CCC  CGA  GAC  CGA  CAT  GAA  GGG  CGC  AAA  CAG  AGC  ACT  ACT  GAG  GCC      6048
Thr  Pro  Arg  Asp  Arg  His  Glu  Gly  Arg  Lys  Gln  Ser  Thr  Thr  Glu  Ala
               2005                     2010                     2015

CAG  AAG  AAA  GCA  GCT  CCA  GCT  TCT  ACT  AAA  CAG  GCT  GAC  CGG  CGC  CAG      6096
Gln  Lys  Lys  Ala  Ala  Pro  Ala  Ser  Thr  Lys  Gln  Ala  Asp  Arg  Arg  Gln
          2020                     2025                     2030

TCG  ATG  GCC  TTC  AGC  ATC  CTC  AAC  ACA  CCC  AAG  AAG  CTA  GGG  AAC  AGC      6144
Ser  Met  Ala  Phe  Ser  Ile  Leu  Asn  Thr  Pro  Lys  Lys  Leu  Gly  Asn  Ser
               2035                     2040                     2045

CTT  CTG  CGG  CGG  GGA  GCC  TCA  AAG  AAG  GCC  CTG  TCC  AAG  GCT  TCC  CCC      6192
Leu  Leu  Arg  Arg  Gly  Ala  Ser  Lys  Lys  Ala  Leu  Ser  Lys  Ala  Ser  Pro
2050                     2055                     2060

AAC  ACT  CGC  AGT  GGA  ACC  CGC  CGT  TCT  CCG  CGC  ATT  GCC  ACC  ACC  ACA      6240
Asn  Thr  Arg  Ser  Gly  Thr  Arg  Arg  Ser  Pro  Arg  Ile  Ala  Thr  Thr  Thr
2065                     2070                     2075                     2080

GCC  AGT  GCC  GCC  ACT  GCT  GCC  GCC  ATT  GGT  GCC  ACC  CCT  CGA  GCC  AAG      6288
Ala  Ser  Ala  Ala  Thr  Ala  Ala  Ala  Ile  Gly  Ala  Thr  Pro  Arg  Ala  Lys
                    2085                     2090                     2095

GGC  AAG  GCA  AAG  CAC  TAA                                                       6306
Gly  Lys  Ala  Lys  His
                    2100
```

( 2 ) INFORMATION FOR SEQ ID NO:4:

( i ) SEQUENCE CHARACTERISTICS:
        ( A ) LENGTH: 2101 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Thr  Leu  His  Ala  Thr  Arg  Gly  Ala  Ala  Leu  Leu  Ser  Trp  Val  Asn
1                        5                        10                       15

Ser  Leu  His  Val  Ala  Asp  Pro  Val  Glu  Ala  Val  Leu  Gln  Leu  Gln  Asp
                    20                       25                       30

Cys  Ser  Ile  Phe  Ile  Lys  Ile  Ile  Asp  Arg  Ile  His  Gly  Thr  Glu  Glu
               35                       40                       45

Gly  Gln  Gln  Ile  Leu  Lys  Gln  Pro  Val  Ser  Glu  Arg  Leu  Asp  Phe  Val
          50                       55                       60

Cys  Ser  Phe  Leu  Gln  Lys  Asn  Arg  Lys  His  Pro  Ser  Ser  Pro  Glu  Cys
```

-continued

|  | 65 |  |  |  | 70 |  |  |  | 75 |  |  |  | 80 |  |
|---|---|---|---|---|---|---|---|---|---|---|---|---|---|---|

Leu Val Ser Ala Gln Lys Val Leu Glu Gly Ser Glu Leu Glu Leu Ala
            85                      90                      95

Lys Met Thr Met Leu Leu Leu Tyr His Ser Thr Met Ser Ser Lys Ser
            100                     105                     110

Pro Arg Asp Trp Glu Gln Phe Glu Tyr Lys Ile Gln Ala Glu Leu Ala
            115                     120                     125

Val Ile Leu Lys Phe Val Leu Asp His Glu Asp Gly Leu Asn Leu Asn
        130                     135                 140

Glu Asp Leu Glu Asn Phe Leu Gln Lys Ala Pro Val Pro Ser Thr Cys
145                     150                     155                 160

Ser Ser Thr Phe Pro Glu Glu Leu Ser Pro Pro Ser His Gln Ala Lys
                165                     170                     175

Arg Glu Ile Arg Phe Leu Glu Leu Gln Lys Val Ala Ser Ser Ser Ser
            180                     185                     190

Gly Asn Asn Phe Leu Ser Gly Ser Pro Ala Ser Pro Met Gly Asp Ile
        195                     200                     205

Leu Gln Thr Pro Gln Phe Gln Met Arg Arg Leu Lys Lys Gln Leu Ala
    210                     215                     220

Asp Glu Arg Ser Asn Arg Asp Glu Leu Glu Leu Glu Leu Ala Glu Asn
225                     230                     235                 240

Arg Lys Leu Leu Thr Glu Lys Asp Ala Gln Ile Ala Met Met Gln Gln
                245                     250                     255

Arg Ile Asp Arg Leu Ala Leu Leu Asn Glu Lys Gln Ala Ala Ser Pro
            260                     265                     270

Leu Glu Pro Lys Glu Leu Glu Glu Leu Arg Asp Lys Asn Glu Ser Leu
        275                     280                     285

Thr Met Arg Leu His Glu Thr Leu Lys Gln Cys Gln Asp Leu Lys Thr
    290                     295                     300

Glu Lys Ser Gln Met Asp Arg Lys Ile Asn Gln Leu Ser Glu Glu Asn
305                     310                     315                 320

Gly Asp Leu Ser Phe Lys Leu Arg Glu Phe Ala Ser His Leu Gln Gln
                325                     330                     335

Leu Gln Asp Ala Leu Asn Glu Leu Thr Glu Glu His Ser Lys Ala Thr
            340                     345                     350

Gln Glu Trp Leu Glu Lys Gln Ala Gln Leu Glu Lys Glu Leu Ser Ala
        355                     360                     365

Ala Leu Gln Asp Lys Lys Cys Leu Glu Glu Lys Asn Glu Ile Leu Gln
    370                     375                     380

Gly Lys Leu Ser Gln Leu Glu Glu His Leu Ser Gln Leu Gln Asp Asn
385                     390                     395                 400

Pro Pro Gln Glu Lys Gly Glu Val Leu Gly Asp Val Leu Gln Leu Glu
                405                     410                     415

Thr Leu Lys Gln Glu Ala Ala Thr Leu Ala Ala Asn Asn Thr Gln Leu
            420                     425                     430

Gln Ala Arg Val Glu Met Leu Glu Thr Glu Arg Gly Gln Gln Glu Ala
        435                     440                     445

Lys Leu Leu Ala Glu Arg Gly His Phe Glu Glu Lys Gln Gln Leu
    450                     455                     460

Ser Ser Leu Ile Thr Asp Leu Gln Ser Ser Ile Ser Asn Leu Ser Gln
465                     470                     475                 480

Ala Lys Glu Glu Leu Glu Gln Ala Ser Gln Ala His Gly Ala Arg Leu
                485                     490                     495

```
Thr  Ala  Gln  Val  Ala  Ser  Leu  Thr  Ser  Glu  Leu  Thr  Thr  Leu  Asn  Ala
               500                 505                      510
Thr  Ile  Gln  Gln  Gln  Asp  Gln  Glu  Leu  Ala  Gly  Leu  Lys  Gln  Gln  Ala
               515                 520                      525
Lys  Glu  Lys  Gln  Ala  Gln  Leu  Ala  Gln  Thr  Leu  Gln  Gln  Glu  Gln
530                           535                      540
Ala  Ser  Gln  Gly  Leu  Arg  His  Gln  Val  Glu  Gln  Leu  Ser  Ser  Leu
545                 550                      555                      560
Lys  Gln  Lys  Glu  Gln  Gln  Leu  Lys  Glu  Val  Ala  Glu  Lys  Gln  Glu  Ala
                    565                 570                      575
Thr  Arg  Gln  Asp  His  Ala  Gln  Gln  Leu  Ala  Thr  Ala  Ala  Glu  Glu  Arg
               580                 585                      590
Glu  Ala  Ser  Leu  Arg  Glu  Arg  Asp  Ala  Ala  Leu  Lys  Gln  Leu  Glu  Ala
               595                 600                      605
Leu  Glu  Lys  Glu  Lys  Ala  Ala  Lys  Leu  Glu  Ile  Leu  Gln  Gln  Gln  Leu
               610                 615                      620
Gln  Val  Ala  Asn  Glu  Ala  Arg  Asp  Ser  Ala  Gln  Thr  Ser  Val  Thr  Gln
625                           630                      635                 640
Ala  Gln  Arg  Glu  Lys  Ala  Glu  Leu  Ser  Arg  Lys  Val  Glu  Glu  Leu  Gln
                    645                 650                           655
Ala  Cys  Val  Glu  Thr  Ala  Arg  Gln  Glu  Gln  His  Glu  Ala  Gln  Ala  Gln
                    660                 665                      670
Val  Ala  Glu  Leu  Glu  Leu  Gln  Leu  Arg  Ser  Glu  Gln  Gln  Lys  Ala  Thr
               675                 680                      685
Glu  Lys  Glu  Arg  Val  Ala  Gln  Glu  Lys  Asp  Gln  Leu  Gln  Glu  Gln  Leu
     690                      695                 700
Gln  Ala  Leu  Lys  Glu  Ser  Leu  Lys  Val  Thr  Lys  Gly  Ser  Leu  Glu  Glu
705                      710                 715                           720
Glu  Lys  Arg  Arg  Ala  Ala  Asp  Ala  Leu  Glu  Glu  Gln  Gln  Arg  Cys  Ile
                    725                 730                      735
Ser  Glu  Leu  Lys  Ala  Glu  Thr  Arg  Ser  Leu  Val  Glu  Gln  His  Lys  Arg
               740                 745                      750
Glu  Arg  Lys  Glu  Leu  Glu  Glu  Glu  Arg  Ala  Gly  Arg  Lys  Gly  Leu  Glu
          755                      760                 765
Ala  Arg  Leu  Leu  Gln  Leu  Gly  Glu  Ala  His  Gln  Ala  Glu  Thr  Glu  Val
770                           775                      780
Leu  Arg  Arg  Glu  Leu  Ala  Glu  Ala  Met  Ala  Ala  Gln  His  Thr  Ala  Glu
785                      790                 795                           800
Ser  Glu  Cys  Glu  Gln  Leu  Val  Lys  Glu  Val  Ala  Ala  Trp  Arg  Asp  Gly
                    805                 810                      815
Tyr  Glu  Asp  Ser  Gln  Gln  Glu  Glu  Ala  Gln  Tyr  Gly  Ala  Met  Phe  Gln
               820                 825                      830
Glu  Gln  Leu  Met  Thr  Leu  Lys  Glu  Glu  Cys  Glu  Lys  Ala  Arg  Gln  Glu
               835                 840                      845
Leu  Gln  Glu  Ala  Lys  Glu  Lys  Val  Ala  Gly  Ile  Glu  Ser  His  Ser  Glu
     850                      855                 860
Leu  Gln  Ile  Ser  Arg  Gln  Gln  Asn  Lys  Leu  Ala  Glu  Leu  His  Ala  Asn
865                      870                      875                      880
Leu  Ala  Arg  Ala  Leu  Gln  Gln  Val  Gln  Glu  Lys  Glu  Val  Arg  Ala  Gln
                    885                 890                      895
Lys  Leu  Ala  Asp  Asp  Leu  Ser  Thr  Leu  Gln  Glu  Lys  Met  Ala  Ala  Thr
               900                 905                      910
Ser  Lys  Glu  Val  Ala  Arg  Leu  Glu  Thr  Leu  Val  Arg  Lys  Ala  Gly  Glu
               915                 920                      925
```

```
Gln Gln Glu Thr Ala Ser Arg Glu Leu Val Lys Glu Pro Ala Arg Ala
    930                 935                 940

Gly Asp Arg Gln Pro Glu Trp Leu Glu Glu Gln Gly Arg Gln Phe
945                 950                 955                 960

Cys Ser Thr Gln Ala Ala Leu Gln Ala Met Glu Arg Glu Ala Glu Gln
                965                 970                 975

Met Gly Asn Glu Leu Glu Arg Leu Arg Ala Ala Leu Met Glu Ser Gln
            980                 985                 990

Gly Gln Gln Gln Glu Glu Arg Gly Gln Gln Glu Arg Glu Val Ala Arg
        995                 1000                1005

Leu Thr Gln Glu Arg Gly Arg Ala Gln Ala Asp Leu Ala Leu Glu Lys
    1010                1015                1020

Ala Ala Arg Ala Glu Leu Glu Met Arg Leu Gln Asn Ala Leu Asn Glu
1025                1030                1035                1040

Gln Arg Val Glu Phe Ala Thr Leu Gln Glu Ala Leu Ala His Ala Leu
                1045                1050                1055

Thr Glu Lys Glu Gly Lys Asp Gln Glu Leu Ala Lys Leu Arg Gly Leu
                1060                1065                1070

Glu Ala Ala Gln Ile Lys Glu Leu Glu Glu Leu Arg Gln Thr Val Lys
            1075                1080                1085

Gln Leu Lys Glu Gln Leu Ala Lys Lys Glu Lys Glu His Ala Ser Gly
    1090                1095                1100

Ser Gly Ala Gln Ser Glu Ala Ala Gly Arg Thr Glu Pro Thr Gly Pro
1105                1110                1115                1120

Lys Leu Glu Ala Leu Arg Ala Glu Val Ser Lys Leu Glu Gln Gln Cys
                1125                1130                1135

Gln Lys Gln Gln Gln Gln Ala Asp Ser Leu Glu Arg Ser Leu Glu Ala
            1140                1145                1150

Glu Arg Ala Ser Arg Ala Glu Arg Asp Ser Ala Leu Glu Thr Leu Gln
        1155                1160                1165

Gly Gln Leu Glu Glu Lys Ala Gln Glu Leu Gly His Ser Gln Ser Ala
    1170                1175                1180

Leu Ala Ser Ala Gln Arg Glu Leu Ala Ala Phe Arg Thr Lys Val Gln
1185                1190                1195                1200

Asp His Ser Lys Ala Glu Asp Glu Trp Lys Ala Gln Val Ala Arg Gly
                1205                1210                1215

Arg Gln Glu Ala Glu Arg Lys Asn Ser Leu Ile Ser Ser Leu Glu Glu
            1220                1225                1230

Glu Val Ser Ile Leu Asn Arg Gln Val Leu Glu Lys Glu Gly Glu Ser
        1235                1240                1245

Lys Glu Leu Lys Arg Leu Val Met Ala Glu Ser Glu Lys Ser Gln Lys
    1250                1255                1260

Leu Glu Glu Ser Cys Ala Cys Cys Arg Gln Arg Gln Pro Ala Thr Val
1265                1270                1275                1280

Pro Glu Leu Gln Asn Ala Ala Leu Leu Cys Gly Arg Arg Cys Arg Ala
                1285                1290                1295

Ser Gly Arg Glu Ala Glu Lys Gln Arg Val Ala Ser Glu Asn Leu Arg
            1300                1305                1310

Gln Glu Leu Thr Ser Gln Ala Glu Arg Ala Glu Glu Leu Gly Gln Glu
        1315                1320                1325

Leu Lys Ala Trp Gln Glu Lys Phe Phe Gln Lys Glu Gln Ala Leu Ser
    1330                1335                1340

Thr Leu Gln Leu Glu His Thr Ser Thr Gln Ala Leu Val Ser Glu Leu
```

```
      1345                1350                1355                1360
Leu Pro Ala Lys His Leu Cys Gln Gln Leu Gln Ala Glu Gln Ala Ala
                1365                1370                1375
Ala Glu Lys Arg His Arg Glu Glu Leu Gln Ser Lys Gln Ala Ala
                1380                1385                1390
Gly Gly Leu Arg Ala Glu Leu Leu Arg Ala Gln Arg Glu Leu Gly Glu
                1395                1400                1405
Leu Ile Pro Leu Arg Gln Lys Val Ala Gln Glu Arg Thr Ala Gln
     1410                1415                1420
Gln Leu Arg Ala Glu Lys Ala Ser Tyr Ala Glu Gln Leu Ser Met Leu
1425                1430                1435                1440
Lys Lys Ala His Gly Leu Leu Ala Glu Glu Asn Arg Gly Leu Gly Glu
                1445                1450                1455
Arg Ala Asn Leu Gly Arg Gln Phe Leu Glu Val Glu Leu Asp Gln Ala
                1460                1465                1470
Arg Glu Lys Tyr Val Gln Glu Leu Ala Ala Val Arg Ala Asp Ala Glu
                1475                1480                1485
Thr Arg Leu Ala Glu Val Gln Arg Glu Ala Gln Ser Thr Ala Arg Glu
                1490                1495                1500
Leu Glu Val Met Thr Ala Lys Tyr Glu Gly Ala Lys Val Lys Val Leu
1505                1510                1515                1520
Glu Glu Arg Gln Arg Phe Gln Glu Glu Arg Gln Lys Leu Thr Ala Gln
                1525                1530                1535
Val Glu Glu Leu Ser Lys Lys Leu Ala Asp Ser Asp Gln Ala Ser Lys
                1540                1545                1550
Val Gln Gln Gln Lys Leu Lys Ala Val Gln Ala Gln Gly Gly Glu Ser
                1555                1560                1565
Gln Gln Glu Ala Gln Arg Phe Gln Ala Gln Leu Asn Glu Leu Gln Ala
                1570                1575                1580
Gln Leu Ser Gln Lys Glu Gln Ala Ala Glu His Tyr Lys Leu Gln Met
1585                1590                1595                1600
Glu Lys Ala Lys Thr His Tyr Asp Ala Lys Lys Gln Gln Asn Gln Glu
                1605                1610                1615
Leu Gln Glu Gln Leu Arg Ser Leu Glu Gln Leu Gln Lys Glu Asn Lys
                1620                1625                1630
Glu Leu Arg Ala Glu Ala Glu Arg Leu Gly His Glu Leu Gln Gln Ala
                1635                1640                1645
Gly Leu Lys Thr Lys Glu Ala Glu Gln Thr Cys Arg His Leu Thr Ala
                1650                1655                1660
Gln Val Arg Ser Leu Glu Ala Gln Val Ala His Ala Asp Gln Gln Leu
1665                1670                1675                1680
Arg Asp Leu Gly Lys Phe Gln Val Ala Thr Asp Ala Leu Lys Ser Arg
                1685                1690                1695
Glu Pro Gln Ala Lys Pro Gln Leu Asp Leu Ser Ile Asp Ser Leu Asp
                1700                1705                1710
Leu Ser Cys Glu Glu Gly Thr Pro Leu Ser Ile Thr Ser Lys Leu Pro
                1715                1720                1725
Arg Thr Gln Pro Asp Gly Thr Ser Val Pro Gly Glu Pro Ala Ser Pro
                1730                1735                1740
Ile Ser Gln Arg Leu Pro Pro Lys Val Glu Ser Leu Glu Ser Leu Tyr
1745                1750                1755                1760
Phe Thr Pro Ile Pro Ala Arg Ser Gln Ala Pro Leu Glu Ser Ser Leu
                1765                1770                1775
```

```
Asp  Ser  Leu  Gly  Asp  Val  Phe  Leu  Asp  Ser  Gly  Arg  Lys  Thr  Arg  Ser
               1780                1785                1790

Ala  Arg  Arg  Arg  Thr  Thr  Gln  Ile  Ile  Asn  Ile  Thr  Met  Thr  Lys  Lys
               1795                1800                1805

Leu  Asp  Val  Glu  Glu  Pro  Asp  Ser  Ala  Asn  Ser  Ser  Phe  Tyr  Ser  Thr
     1810                1815                1820

Arg  Ser  Ala  Pro  Ala  Ser  Gln  Ala  Ser  Leu  Arg  Ala  Thr  Ser  Ser  Thr
1825                1830                1835                          1840

Gln  Ser  Leu  Ala  Arg  Leu  Gly  Ser  Pro  Asp  Tyr  Gly  Asn  Ser  Ala  Leu
                    1845                1850                          1855

Leu  Ser  Leu  Pro  Gly  Tyr  Arg  Pro  Thr  Thr  Arg  Ser  Ser  Ala  Arg  Arg
               1860                1865                     1870

Ser  Gln  Ala  Gly  Val  Ser  Ser  Gly  Ala  Pro  Pro  Gly  Arg  Asn  Ser  Phe
          1875                1880                     1885

Tyr  Met  Gly  Thr  Cys  Gln  Asp  Glu  Pro  Glu  Gln  Leu  Asp  Asp  Trp  Asn
          1890                1895                     1900

Arg  Ile  Ala  Glu  Leu  Gln  Gln  Arg  Asn  Arg  Val  Cys  Pro  Pro  His  Leu
1905                     1910                1915                          1920

Lys  Thr  Cys  Tyr  Pro  Leu  Glu  Ser  Arg  Pro  Ser  Leu  Ser  Leu  Gly  Thr
                    1925                1930                     1935

Ile  Thr  Asp  Glu  Glu  Met  Lys  Thr  Gly  Asp  Pro  Gln  Glu  Thr  Leu  Arg
               1940                1945                1950

Arg  Ala  Ser  Met  Gln  Pro  Ile  Gln  Ile  Ala  Glu  Gly  Thr  Gly  Ile  Thr
               1955                1960                1965

Thr  Arg  Gln  Gln  Arg  Lys  Arg  Val  Ser  Leu  Glu  Pro  His  Gln  Gly  Pro
     1970                1975                1980

Gly  Thr  Pro  Glu  Ser  Lys  Lys  Ala  Thr  Ser  Cys  Phe  Pro  Arg  Pro  Met
1985                1990                     1995                          2000

Thr  Pro  Arg  Asp  Arg  His  Glu  Gly  Arg  Lys  Gln  Ser  Thr  Thr  Glu  Ala
               2005                2010                     2015

Gln  Lys  Lys  Ala  Ala  Pro  Ala  Ser  Thr  Lys  Gln  Ala  Asp  Arg  Arg  Gln
               2020                2025                2030

Ser  Met  Ala  Phe  Ser  Ile  Leu  Asn  Thr  Pro  Lys  Lys  Leu  Gly  Asn  Ser
               2035                2040                2045

Leu  Leu  Arg  Arg  Gly  Ala  Ser  Lys  Lys  Ala  Leu  Ser  Lys  Ala  Ser  Pro
2050                     2055                     2060

Asn  Thr  Arg  Ser  Gly  Thr  Arg  Arg  Ser  Pro  Arg  Ile  Ala  Thr  Thr  Thr
2065                2070                     2075                          2080

Ala  Ser  Ala  Ala  Thr  Ala  Ala  Ala  Ile  Gly  Ala  Thr  Pro  Arg  Ala  Lys
               2085                2090                     2095

Gly  Lys  Ala  Lys  His
               2100
```

( 2 ) INFORMATION FOR SEQ ID NO:5:

( i ) SEQUENCE CHARACTERISTICS:
        ( A ) LENGTH: 353 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: mRNA
        ( B ) LOCATION: 1..353
        ( D ) OTHER INFORMATION: /note= "ANTI-SENSE SEQUENCE TO PART OF THE MTI MRNA TRANSCRIPT: N TERMINUS OF PROTEIN CODING SEQUENCE AND UPSTREAM 53 NUCLEOTIDES"

( i x ) FEATURE:
     ( A ) NAME/KEY: misc_feature
     ( B ) LOCATION: 298..300
     ( D ) OTHER INFORMATION: /note= "MTI INITIATION CODON
           SEQUENCE ON COMPLEMENTARY STRAND"

( x i ) SEQUENCE DESCRIPTION: SEQ ID NO:5:

| | | | | | | |
|---|---|---|---|---|---|---|
| CTCAATTTTA | ACTTGTTCTT | GTTTTTCTCG | TTGTGCAAGG | CGAGCTGCAA | CTTCTTCAGG | 60 |
| TGGTCGCTCC | CTTATAGAAG | ATGAGGATGC | TTCTGAAAGT | GCAGGTGTGG | GTTTTCCTTC | 120 |
| ACCAATTTCA | GGGTGATCAG | TTTTTAAAGA | TTCCTCAGGC | TGAACTGCAG | GGGCTGGGAC | 180 |
| CGACAGGGTA | TCACCTGCTG | CAGAAATAAT | TTGAGCCGCT | TCTGTAGGTG | CTGTTGCTGA | 240 |
| AGCTGGAGTA | TCTCCCTTTT | GTTGTTGGAG | TTGTGAGGCA | GGCTGTTTAG | ATTCTTTCAT | 300 |
| TACTTCTGAT | ACACTAGAGA | TTTTTAGTGG | ACCCGACTGA | ATCGATTTCT | TTG | 353 |

( 2 ) INFORMATION FOR SEQ ID NO:6:

( i ) SEQUENCE CHARACTERISTICS:
           ( A ) LENGTH: 348 base pairs
           ( B ) TYPE: nucleic acid
           ( C ) STRANDEDNESS: single
           ( D ) TOPOLOGY: linear ( i i ) MOLECULE TYPE: cDNA ( i x ) FEATURE:
           ( A ) NAME/KEY: mRNA
           ( B ) LOCATION: 1..348
           ( D ) OTHER INFORMATION: /note= "ANTISENSE SEQUENCE TO PART
                 OF MT2 TRANSCRIPT: N TERMINUS OF PROTEIN CODING
                 REGION AND UPSTREAM 48 NUCLEOTIDE"

( i x ) FEATURE:
           ( A ) NAME/KEY: misc_feature
           ( B ) LOCATION: 298..300
           ( D ) OTHER INFORMATION: /note= "MT2 INITIATION CODON
                 SEQUENCE ON COMPLEMENTARY STRAND"

( x i ) SEQUENCE DESCRIPTION: SEQ ID NO:6:

| | | | | | | |
|---|---|---|---|---|---|---|
| CATGGTCATC | TTCGCCAGTT | CCAGCTCTGA | TCCCTCTAGC | ACCTTCTGTG | CAGATACCAG | 60 |
| GCGTTCTGGG | GAAGAGGGAT | GTTTTCGATT | TTTCTGCAGA | AAACTGCACA | CAAAGTCCAG | 120 |
| TCTCTCTGAC | ACCGGCTGCT | TCTTGATTTG | CTGTCCCTCT | TCAGTGCCAT | GGATTCTGTC | 180 |
| AATGATCTTG | ATGAAGATGC | TGCAGTCCTG | GAGCTGCAGC | ACAGCCTCCA | CAGGGTCAGC | 240 |
| CACGTGTAGA | CTGTTCACCC | AAGAGAGGAG | TGCAGCCCCC | CGGGTGGCGT | GGAGTGTCAT | 300 |
| CTTGGTGATG | CCAGACAGTC | ACTCCAATGC | GCCTGTAATC | CCAGCTAC | | 348 |

MALIGNANT CELL TYPE MARKERS OF THE INTERIOR NUCLEAR MATRIX

This application is a continuation of U.S. Ser. No. 08/195,487, filed Feb. 14, 1994, now U.S. Pat. No. 5,783,403 which is a continuation of U.S. Ser. No. 07/901,701, filed Jun. 22, 1992, now abandoned.

REFERENCE TO RELATED APPLICATIONS

Related applications include: U.S. Ser. No. 08/195,487, filed Feb. 14, 1994, which is a continuation of U.S. Ser. No. 07/901,701, filed Jun. 22, 1992, now abandoned; U.S. Ser. No. 08/466,390, filed Jun. 6, 1995, which is a divisional of U.S. Ser. No. 08/195,487, filed Feb. 14, 1994, which is a continuation of U.S. Ser. No. 07/901,701, filed Jun. 22, 1992, now abandoned; U.S. Ser. No. 08/470,950, filed Jun. 6, 1995, which is a divisional of U.S. Ser. No. 08/195,487, filed Feb. 14, 1994, which is a continuation of U.S. Ser. No. 07/901,701, filed Jun. 22, 1992, now abandoned; U.S. Ser. No. 08/467,781, filed Jun. 6, 1995, which is a divisional of U.S. Ser. No. 08/195,487, filed Feb. 14, 1994, which is a continuation of U.S. Ser. No. 07/901,701, filed Jun. 22, 1992, now abandoned; U.S. Ser. No. 08/456,620, filed Jun. 1, 1995, which is a continuation of U.S. Ser. No. 08/112,646, filed Aug. 26, 1993, now abandoned, which is a continuation of U.S. Ser. No. 07/785,804, filed Oct. 31, 1991, now abandoned; U.S. Ser. No. 08/444,821, filed May 18, 1995, which is a divisional of U.S. Ser. No. 08/112,646, filed Aug. 26, 1993, now abandoned, which is a continuation of U.S. Ser. No. 07/785,804, filed Oct. 31, 1991, now abandoned; and U.S. Ser. No. 08/443,630, filed May 18, 1995, which is a divisional of U.S. Ser. No. 08/112,646, filed Aug. 26, 1993, now abandoned, which is a continuation of U.S. Ser. No. 07/785,804, filed Oct. 31, 1991, now abandoned.

BACKGROUND OF THE INVENTION

All eucaryotic cells, both plant and animal, have a nucleus surrounded by the cell cytoplasm. The nucleus contains the cellular DNA complexed with protein and termed chromatin. The chromatin, with its associated proteins, constitutes the major portion of the nuclear mass and is organized by the internal protein skeleton of the nucleus, referred to here as the nuclear matrix (NM). The nuclear matrix also is defined as the nuclear structure that remains following removal of the chromatin by digestion with DNase I and extraction with high salt. This skeletal nuclear structure further is characterized by the "interior nuclear matrix" (INM) and the bounding nuclear pore-lamina complex.

Diverse studies have implicated the NM in a wide variety of nuclear functions fundamental to the control of gene expression (For a general review see, for example, Fey et al. (1991) Crit. Rev. Euk. Gene Express 1:127–143). In particular, as described in U.S. Pat. Nos. 4,882,268 and 4,885,236, it is now known that certain nuclear matrix proteins, specifically interior nuclear matrix proteins, are useful as marker proteins for identifying cell types. For example, the presence and abundance of particular INM proteins have been shown to be characteristic of specific cell types and can be used to identify the tissue of origin of a cell or cell fragment present in a sample. One particularly important application of this discovery is the use of marker INM proteins in evaluating metastatic tissue. It is also known that the expression of certain INM proteins is altered in malignant or otherwise dysfunctional cells. The altered expression pattern of these proteins in malignant and/or dysfunctioning cells also makes the proteins and nucleic acids encoding the proteins useful as marker proteins, alone or in combination, for diagnostic purposes and for evaluating tissue viability. U.S. Pat. Nos. 4,882,628 and 4,885,236, issued Nov. 21, 1989 and Dec. 5, 1989, respectively, to Penman and Fey, disclose a method for selectively extracting insoluble INM proteins and their associated nucleic acids from cells or cellular debris and distinguishing the expression pattern of these proteins in a particular cell type by displaying the proteins on a two-dimensional electrophoresis gel. In addition, it recently has been discovered that INM proteins or protein fragments also may be released in soluble form from dying cells. (See PCT Publication WO93/09437, published May 13, 1993).

To date, molecular characterization of the specific proteins of the NM, particularly the INM, remain poorly defined due to the low abundance of these proteins in the cell and their generally insoluble character. The ability to isolate and characterize specific nuclear matrix proteins and the genetic sequences encoding them at the molecular level is anticipated to enhance the use of these proteins and their nucleic acids as marker molecules, and to enhance elucidation of the biological role of these proteins in vivo.

It is an object of this invention to provide genetic sequences encoding INM proteins useful as markers of malignant cell types. Another object is to provide enhanced means for identifying these proteins and their nucleic acids, including RNA transcripts, in samples. Yet another object of this invention is to provide compositions for use in diagnostic and other tissue evaluative procedures. Still another object is to provide genetic and amino acid sequences useful as target molecules in a cancer therapy. These and other objects and features of the invention will be apparent from the description, figures and claims which follow.

SUMMARY OF THE INVENTION

Molecular characterization data, including DNA sequence data, for two INM proteins now have been derived from an expression library, using monoclonal antibodies for these proteins. The proteins, designated herein as MT1 and MT2, are present at elevated levels in malignant tissue and extracellular fluids. Accordingly, the proteins and the genetic sequences encoding them are thought to be useful as marker molecules for identifying tissue tumorgenesis in cell or body fluid samples.

Full or partial clones of the genes encoding these proteins now have been isolated, and the DNA sequence, reading frames and encoded amino acid sequences of these DNAs determined. The DNA sequence for MT2 corresponds to the sequence disclosed by Yang, et al. (1992) J. Cell Biol. 116:1303–1317, and Compton et al. (1992) J. Cell Biol. 116:1395–1408, referred to therein as NuMA. The nucleic acid (and the encoded amino acid sequence) described herein for MT1 has not been described previously and also constitutes a novel sequence sharing little sequence homology with those sequences known in the art. In addition, MT1 has been subcloned into an expression vector, and the protein expressed as a cleavable fusion protein in E. coli. Both the MT1 and MT2 (NuMA) proteins are distributed throughout the nucleus (with the exception of the nucleolus) in non-mitotic cells, and localize to the spindle during mitosis, as determined immunofluoresence.

The genetic sequences described herein provide a family of proteins for each of the proteins MT1 and MT2, including allelic and species variants of MT1 and MT2. The family of proteins include these proteins produced by expression in a host cell from recombinant DNA, the DNA itself, and the host cells harboring and capable of expressing these nucleic acids. The recombinantly produced proteins may be isolated using standard methodologies such as affinity chromatography to yield substantially pure proteins. As used herein, "substantially pure" is understood to mean substantially free of undesired, contaminating proteinaceous material.

The family of proteins defined by MT1 includes proteins encoded by the nucleic acid sequence of Seq. ID No. 1, including analogs thereof. As used herein, "analog" is understood to include allelic and species variants, and other naturally-occurring and engineered mutants. Particularly envisioned are DNAs having a different preferred codon usage, those having "silent mutations" of the DNA of Seq. ID No.1, wherein the changes in the genetic sequence do not affect the encoded amino acid sequence, and DNAs encoding "conservative" amino acid changes, as defined by Dayoff et al., *Atlas of Protein Sequence and Structure;* vol. 5, Supp. 3, pp 345–362 (M. O. Dayoff, ed., Nat'l Biomed. Research Foundation, Washington, D.C. 1979.)

Accordingly, the nucleic acids encoding the protein family of MT1 may be defined as those sequences which hybridize to the DNA sequence of Seq. ID No.1 under stringent hybridization conditions. As used herein, stringent hybridization conditions are as defined in *Molecular Cloning: A Laboratory Manual,* Maniatis, et al. eds., Cold Spring Harbor Press, 1985, e.g.: hybridization in 50% formamide, 5× Denhardt's Solution, 5×SSPE, 0.1% SDS and 100 $\mu$g/ml denatured salmon sperm, and washing in 2×SSC, 0.1% SDS, at 37° C., and 1×SSC, 0.1% SDS at 68° C.

The family of proteins defined by MT2 includes proteins encoded by the nucleic acid sequence of Seq. ID No. 3, including analogs thereof, including allelic and species variants, and other naturally-occurring and engineered mutants. Particularly envisioned are DNAs having silent mutations, other preferred codon usages, and DNAs encoding conservative amino acid changes. The nucleic acids encoding the protein family of MT2 of this invention may be defined as those sequences which hybridize with the DNA sequence of Seq. ID No. 3 under stringent hybridization conditions.

In another aspect, the invention provides nucleic acid fragments ("oligonucleotides" or "oligomers") which hybridize to genetic sequences encoding MT1, but which do not necessarily encode functional proteins themselves. The oliognucleotides include probes for isolating genetic sequences encoding members of the MT1 family of proteins from a cDNA or genomic DNA library, and/or for identifying genetic sequences naturally associated with the MT1 protein coding sequence e.g., sequences lying upstream or downstream from the coding sequences. For example, where the nucleic acid fragment is to be used as a probe to identify other members of the MT1 family, the nucleic acid fragment may be a degenerate sequence as described in *Molecular Cloning: A Laboratory Manual,* Maniatis, et al. eds., Cold Spring Harbor Press, 1985, designed using the sequence of Seq. ID No.1 as a template. Accordingly, the oligonucleotide or nucleic acid fragment may comprise part or all of the DNA sequence of Seq. ID No. 1, or may be a biosynthetic sequence based on the DNA sequence of Seq. ID No. 1. The oligonucleotide preferably is suitably labelled using conventional labelling techniques.

The oligonucleotides also include sequences which hybridize with the mRNA transcript encoding the MT1 protein. These complementary sequences are referred to in the art and herein as antisense sequences. Antisense sequences may comprise part or all of the sequence of Seq. ID No. 1, or they may be biosynthetic sequences designed using the sequence of Seq. ID No. 1 as a template.

In still another aspect, the invention provides oligonucleotides which hybridize to the genetic sequences encoding members of the MT2 protein family. The fragments include antisense sequences and sequences useful as probes for identifying members of the MT2 family and/or for identifying associated noncoding sequences. The hybridizing nucleic acids may comprise part or all of the sequence of Seq. ID No. 3 or may be biosynthetic sequences designed using the DNA sequence of Seq. ID No. 3 as a template, preferably suitably labelled using conventional techniques.

The genetic sequences identified herein encode proteins identified as marker proteins indicative of a malignancy or other cellular dysfunction in a tissue. Thus, in another aspect, the invention provides compositions for obtaining antibodies useful for detecting cancer marker proteins in a sample using the proteins described herein in combination with a suitable adjuvant. In another aspect, the invention provides genetic templates for designing sequences which hybridize specifically with the mRNA transcripts encoding these proteins. In still another aspect, the invention provides isolated DNA sequences for use in expressing proteins and protein fragments for the design of binding proteins, including antibodies, which interact specifically with an epitope on MT1 or MT2. The invention also provides methods for evaluating the status of a tissue using the genetic sequences described herein, and the marker proteins encoded by them. Finally, the invention provides methods for treating a malignancy in an individual using these marker proteins, or the genetic sequences encoding them, as target molecules to inhibit or disable the cell's ability to undergo cell division.

BRIEF DESCRIPTION OF THE DRAWINGS

FIGS. 1A–1D is a schematic representation of the amino acid sequence of MT1 of Seq. ID No.1, showing:

FIG. 1A the location of the proline residues;

FIG. 1B the areas defined as $\alpha$-helices within the sequence;

FIG. 1C the location of the cysteine residues; and

FIG. 1D the sites of cleavage by NTCB; and

FIGS. 2A–2B is a schematic representation of the amino acid sequence of MT2 of Seq. ID No.3, showing:

FIG. 2A the location of proline residues; and

FIG. 2B the areas defined as $\alpha$-helices within the sequence.

DETAILED DESCRIPTION

In an attempt to characterize INM proteins useful as malignant cell markers in biological assays, the genetic sequences encoding two INM proteins, herein referred to as MT1 and MT2, now have been identified and characterized. DNA sequences encoding these proteins now have been cloned by probing expression libraries using monoclonal antibodies raised against the isolated INM proteins MT1 and MT2. The proteins were isolated from malignant cells essentially following the method of Penman and Fey, described in U.S. Pat. Nos. 4,882,268 and 4,885,236, the disclosures of which are herein incorporated by reference. The cloned DNAs, then were sequenced and their reading frames identified and analyzed. The genetic sequence encoding MT2 also has been disclosed by others (Yang, et al. (1992) *J. Cell Biol.* 116:1303–1317 and Compton et al. (1992) *J. Cell. Biol.* 116:1395–1408), and is referred to by them as "NuMA". Comparison of MT1 and MT2 (NuMA)

with other sequences in the art indicate that the sequences encoding these proteins constitute sequences sharing little homology with previously described sequences.

MT1 also has been expressed as a cleavable fusion protein in *E. coli* and compared with the protein isolated from mammalian cells. Anti-MT1 antibodies raised against the natural-sourced MT1 protein also crossreact with the recombinantly produced protein. Both the natural-sourced and recombinantly produced proteins have the same apparent molecular weight when analyzed by SDS-PAGE (90 kD), equivalent pI values (5.4), and both proteins show the same cleavage pattern when cleaved with 2-nitro-3-thiocyanobenzoic acid (NTCB, see infra.)

Immunolocalization data on MT1 indicates that MT1 protein is distributed within the INM in non-mitotic cells as discrete punctate foci, nonuniformly distributed throughout the nucleoplasm of the INM. Specifically, the foci are present in the interchromatinic regions of the nucleus and are distributed in a stable association that remains after chromatin extraction, as is anticipated for an interior nuclear matrix protein. In addition, MT1 foci are excluded from the nucleolus and the nuclear lamina. Moreover, during mitosis, the distribution of MT1 changes and MT1 becomes aligned in a stellate or star-shaped pattern at the spindle of the dividing cell. The protein does not co-localize with the chromosomes, suggesting that MT1 may play a structural role during mitosis. The immunolocalization data is consistent with the MT1 amino acid sequence analysis data which fails to find structural homology with any known DNA binding motifs, such as the "leucine zipper."

While the MT2 (NuMA) protein has not yet been recombinantly expressed, the predicted molecular weight of 238 kDa for this protein, calculated from the predicted amino acid sequence (see Seq. ID No. 3), agrees with that of the natural-sourced material.

Immunolocalization studies on MT2 (NuMA) indicate that it also forms punctate foci located throughout the nucleoplasm of the non-mitotic cell, and also is excluded from the nucleolus. During mitosis the protein appears to migrate to the spindle poles of the dividing cell. The primary sequence appears to suggest a coiled-coil motif for the folded protein. (Compton, et al. (1992) *J. Cell Biol.* 116:1395–1408; Yang, et al. (1992) *J. Cell Biol.* 116:1303–1317.)

I. How to Use

The nucleic acids disclosed herein encode proteins originally identified as marker proteins useful for identifying cell malignancies or other cell abnormalties. Specifically, significantly elevated levels of these proteins are detected in malignant cells and in extracellular fluids, e.g., sera, of cancer patients. (See PCT Publication WO93/09437, published May 13, 1993, the disclosure of which is incorporated herein by reference.) For example, the presence and/or abundance of these proteins or their transcripts in a sample containing cells or cell nuclear debris may be used to determine whether a given tissue comprises malignant cells or cells having other abnormalities, such as chromosomal abnormalities. The sample may be an exfoliated cell sample or a body fluid sample, e.g., a sample comprising blood, serum, plasma, urine, semen, vaginal secretions, spinal fluid, saliva, ascitic fluid, peritoneal fluid, sputum, tissue swabs, and body exudates such as breast exudate.

In addition, because INM proteins are released in soluble form from dying cells, the marker molecules may be used to evaluate the viability of a given tissue. For example, the marker proteins may be used to evaluate the status of a disease or the efficacy of a therapeutic treatment or procedure, by monitoring the release of these marker molecules into a body fluid over a period of time. Particularly useful body fluids include blood, serum, plasma, urine, semen, vaginal secretions, spinal fluid, saliva, ascitic fluid, peritoneal fluid, sputum, tissue swabs, and body exudates such as breast exudate. Methods for performing these assays are disclosed in U.S. Pat. Nos. 4,882,268 and 4,885,236 and in co-pending U.S. application Ser. No. 214,022, filed Jun. 30, 1988, now U.S. Pat. No. 5,273,877, and PCT Publication WO93/09437, published May 13, 1993, the disclosures of which are incorporated herein by reference.

All of these assays are characterized by the following general procedural steps:

1) detecting the presence and/or abundance of the marker protein or its transcript in "authentic" or reference samples;
2) detecting the presence and/or abundance of the marker protein or its transcript in the sample of interest; and
3) comparing the quantity of marker protein or its transcript in the sample of interest with the quantity present in the reference sample.

Where the assay is used to monitor tissue viability, the step of detecting the presence and abundance of the marker protein or its transcript in samples of interest is repeated at intervals and these values then are compared, the changes in the detected concentrations reflecting changes in the status of the tissue. Where the assay is used to evaluate the efficacy of a therapy, the monitoring steps occur following administration of the therapeutic agent or procedure (e.g., following administration of a chemotherapeutic agent or following radiation treatment.)

It is not required that the selected marker protein or transcript be totally unique, in the sense that the particular INM marker molecule is present in the target cell type and in no other. Rather, it is required that the marker molecule have a signal to noise ratio high enough to discriminate the preselected cell type in samples for which the assay is designed. For example, MT1 and MT2 proteins are useful as proteins indicating the presence of malignancy in cell samples because of their elevated expression levels in malignant cells, even though the proteins, or close analogs thereof, may be present commonly in nonmalignant cell types.

A brief description of general protein and nucleic acid assay considerations follows below. Details of particular assay conditions may be found in the assay references described above and incorporated herein by reference, and in published protocols well known in the art and readily available.

A. Protein Assays

Characterization of the MT1 and MT2 proteins at the molecular level as described herein allows one to characterize the proteins structurally and biochemically. Accordingly, following the disclosure of these genetic sequences and their encoded amino acid sequences, preferred binding epitopes may be identified which may be used to enhance assay conditions. For example, binding proteins may be designed which have enhanced affinity for the marker protein produced by particular cell types or as a function of particular malignancies. Similarly, binding proteins may be designed which bind preferentially to protein fragments released from dying cells. In addition, structural and/or sequence variations between proteins produced in normal and abnormal tissue now may be investigated and used to advantage. The genetic sequences may be manipulated as desired, e.g., truncated, mutagenized or the like, using standard recombinant DNA procedures known in the art, to obtained proteins having desired features useful for antibody production.

As will be appreciated by those skilled in the art, any means for specifically identifying and quantifying a marker protein of interest is contemplated. The currently preferred means for detecting a protein of interest in a sample is by means of a binding protein capable of interacting specifically with the marker protein. Labelled antibodies or the binding portions thereof in particular may be used to advantage. The antibodies may be monoclonal or polyclonal in origin, or may be biosynthetically produced. The amount of complexed marker protein, e.g., the amount of marker protein associated with the binding protein, then is determined using standard protein detection methodologies well described in the art.

A.1. Immunoassays

A variety of different forms of immunoassays currently exist, all of which may be adapted to detect and quantitate INM proteins and protein fragments. For exfoliated cell samples, as an example, the cells and surrounding fluid are collected and the INM proteins selectively isolated by the method of Penman and Fey, described in U.S. Pat. Nos. 4,882,268 and 4,885,236. These proteins then preferably are separated by two-dimensional gel electrophoresis and the presence of the marker protein detected by standard Western blot procedures.

For serum and other fluid assays where the marker proteins and/or protein fragments to be detected exist primarily in solution, one of the currently most sensitive immunoassay formats is the sandwich technique. In this method, as described in PCT Publication WO93/09437, published May 13, 1993, two antibodies capable of binding the analyte of interest generally are used: e.g., one immobilized onto a solid support, and one free in solution, but labeled with some easily detectable chemical compound. Examples of chemical labels that may be used for the second antibody include radioisotopes, fluorescent compounds, and enzymes or other molecules which generate colored or electrochemically active products when exposed to a reactant or enzyme substrate. When samples containing the marker protein or protein fragment are placed in this system, the marker protein binds to both the immobilized antibody and the labelled antibody. The result is a "sandwich" immune complex on the support's surface. The complexed protein is detected by washing away nonbound sample components and excess labeled antibody, and measuring the amount of labeled antibody complexed to protein on the support's surface. The sandwich immunoassay is highly specific and very sensitive, provided that labels with good limits of detection are used. A detailed review of immunological assay design, theory and protocols can be found in numerous texts in the art, including *Practical Immunology*, Butt, W. R., ed., Marcel Dekker, New York, 1984.

In general, immunoassay design considerations include preparation of antibodies (e.g., monoclonal or polyclonal) having sufficiently high binding specificity for their antigen that the specifically-bound antibody-antigen complex can be distinguished reliably from nonspecific interactions. As used herein, "antibody" is understood to include other binding proteins having appropriate binding affinity and specificity for the marker protein. The higher the antibody binding specificity, the lower the antigen concentration that can be detected. Currently preferred binding specificity is such that the binding protein has a binding affinity for the marker protein of greater than about $10^5$ $M^{-1}$, preferably greater than about $10^7$ $M^{-1}$.

Antibody binding domains also may be produced biosynthetically and the amino acid sequence of the binding domain manipulated to enhance binding affinity with a preferred epitope. Identification of the genetic sequences for MT1 and MT2 can be used to advantage in the design and construction of preferred binding proteins. For example, a DNA encoding a preferred epitope may be recombinantly expressed and used to select an antibody which binds selectively to the epitope. The selected antibodies then are exposed to the sample under conditions sufficient to allow specific binding of the antibody to its specific nuclear matrix protein or protein fragment, and the amount of complex formed then detected. Specific antibody methodologies are well understood and described in the literature. A more detailed description of their preparation can be found, for example, in *Practical Immunology*, Butt, W. R., ed., Marcel Dekker, New York, 1984.

The choice of tagging label also will depend on the detection limitations desired. Enzyme assays (ELISAs) typically allow detection of a colored product formed by interaction of the enzyme-tagged complex with an enzyme substrate. Alternative labels include radioactive or fluorescent labels. The most sensitive label known to date is a chemiluminescent tag where interaction with a reactant results in the production of light. Useful labels include chemiluminescent molecules such as acridium esters or chemiluminescent enzymes where the reactant is an enzyme substrate. When, for example, acridium esters are reacted with an alkaline peroxide solution, an intense flash of light is emitted, allowing the limit of detection to be increased 100 to 10,000 times over those provided by other labels. In addition, the reaction is rapid. A detailed review of chemiluminescence and immunoassays can be found in Weeks, et al., (1983) *Methods in Enzymology* 133:366–387. Other considerations for fluid assays include the use of microtiter wells or column immunoassays. Column assays may be particularly advantageous where rapidly reacting labels, such as chemiluminescent labels, are used. The tagged complex can be eluted to a post-column detector which also contains the reactant or enzyme substrate, allowing the subsequent product formed to be detected immediately.

A.2. Antibody Production

The proteins described herein may be used to raise antibodies using standard immunological procedures well known and described in the art. See, for example, *Practical Immunology*, Butt, N. R., ed., Marchel Dekker, New York, 1984. Briefly, an isolated INM protein produced, for example, by recombinant DNA expression in a host cell, is used to raise antibodies in a xenogenic host. Preferred antibodies are antibodies that bind specifically to an epitope on the protein, preferably having a binding affinity greater than $10^5$ $M^{-1}$, most preferably having an affinity greater than $10^7$ $M^{-1}$ for that epitope. For example, where antibodies to a human INM protein, e.g. MT1 or MT2 is desired, a suitable antibody generating host is a mouse, goat, rabbit, guinea pig, or other mammal useful for generating antibodies. The protein is combined with a suitable adjuvant capable of enhancing antibody production in the host, and injected into the host, for example, by intraperitoneal administration. Any adjuvant suitable for stimulating the host's immune response may be used to advantage. A currently preferred adjuvant is Freund's complete adjuvant (an emulsion comprising killed and dried microbial cells, e.g., from Calbiochem Corp., San Diego, or Gibco, Grand Island, N.Y.). Where multiple antigen injections are desired, the subsequent injections comprise the antigen in combination with an incomplete adjuvant (e.g. cell-free emulsion).

Polyclonal antibodies may be isolated from the antibody-producing host by extracting serum containing antibodies to the protein of interest. Monoclonal antibodies may be produced by isolating host cells that produce the desired antibody, fusing these cells with myeloma cells using standard procedures known in the immunology art, and screening for hybrid cells (hybridomas) that react specifically with the INM protein and have the desired binding affinity.

Provided below is an exemplary protocol for monoclonal antibody production, which is currently preferred. Other protocols also are envisioned. Accordingly, the particular method of producing antibodies with the cancer marker protein compositions of this invention, is not envisioned to be an aspect of the invention. Also provided are representative assays demonstrating antibody specificity and protein quantification of antigen detected in cell culture supernatants and human sera.

Exemplary antibody production protocol: Balb/c by J mice (Jackson Laboratory, Bar Harbor, Me.) are injected intraperitoneally with purified INM protein (e.g., MT1) purified from the human cervical cell line CaSki, every 2 weeks for a total of 16 weeks. The mice are injected with a single boost 4 days prior to sacrifice and removal of the spleen. Freund's complete adjuvant (Gibco, Grand Island) is used in the first injection, incomplete Freund's in the second injection; subsequent injections are made with saline. Spleen cells (or lymph node cells) then are fused with a mouse myeloma line, e.g., using the method of Kohler and Milstein (1975) *Nature* 256:495, the disclosure of which is incorporated herein by reference, and using polyethylene glycol (PEG, Boehringer Mannheim, Germany). Hybridomas producing antibodies that react with nuclear matrix proteins then are cloned and grown as ascites. Hybridomas are screened by nuclear reactivity against the cell line that is the source of the immunogen, and by tissue immunochemistry using standard procedures known in the immunology art. Detailed descriptions of screening protocols, ascites production and immunoassays also are disclosed in WO93/09437, published May 13, 1993, incorporated hereinabove by reference.

Representative Assays

Table I below displays the binding results for assays performed with different antibodies raised against the two different cervical tumor cell line NM (nuclear matrix) antigen preparations (ME-180 and CaSKi, American Type Culture Collection, ATCC, Rockville, Md.). The 100-series antibodies are those raised against the ME-180 NM immunogen; the 300-series are those raised against CaSKi-NM immunogen.

epitopes on the same molecule. Only one antibody, 302-18, reacted in combination with itself.

Dose Response Assays

The first sandwich assay was obtained using antibodies 200-34 and 200-4 on nuclear matrix proteins isolated by the method of Penman and Fey (Table II) and on cell culture supernatant from dying cells (Table III). The cell line T-47D (breast tumor cell line, ATCC, Rockville, Md.) was used as the source of antigen for both experiments and demonstrated that a dose response curve can be obtained with these assay conditions.

Table II shows the data generated using a standard ELISA immunoassay and purified NM, isolated by the method of Penman et al. Table III shows the data generated under the same conditions, but using the supernatant of dying cells as the antigen source. The cell line T-47D was used as the antigen source for both experiments and two antibodies, previously shown to have strong reactivity with the T-47D antigen by dot blot assay, were used (Ab 200-34, solid phase; Ab 200-4 as soluble antibody).

TABLE II

| | OD | | |
|---|---|---|---|
| Protein Concn. in NM prep. | rep 1 | rep 2 | mean |
| 10 mg/ml | 0.186 | 0.187 | |
| 1 mg/ml | 0.036 | 0.032 | 0.034 |
| 0.1 mg/ml | 0.021 | 0.009 | 0.015 |
| 0.0 | 0.000 | 0.003 | 0.001 |

TABLE III

| Concentration of supernatant | Mean OD | SD |
|---|---|---|
| Undiluted | 0.150 | 0.015 |
| 1:2 | 0.071 | 0.010 |
| 1:4 | 0.026 | 0.003 |
| 1:8 | 0.013 | 0.005 |
| No Sup | | |
| 2:1 | 0.401 | 0.015 |
| undiluted | 0.145 | 0.006 |
| 1:2 | 0.05 | 0.002 |
| 1:4 | 0.017 | 0.003 |
| 1:8 | 0.003 | 0.002 |
| No Sup | 0.000 | |

The data show that reliable dose response curves can be generated using these assay conditions to quantitate soluble NM antigen in solution. Following this protocol, other antibody combinations can be tested for their ability to

TABLE I

| | SOLUTIONS Ab | | | | | |
|---|---|---|---|---|---|---|
| CAPTURE Ab | 107-7 | 302-18 | 302-22 | 302-29 | 302-47 | 307-33 |
| 107-7 | NO RXN | NO RXN | NO RXN | RX | NO RXN | RXN |
| 302-18 | NO RXN | RXN | RXN | RXN | RXN | RXN |
| 302-22 | NO RXN | RXN | NO RXN | NO RXN | NO RXN | RXN |
| 302-29 | NO RXN | RXN | NO RXN | NO RXN | NO RXN | RXN |
| 302-47 | NO RXN | NO RXN | NO RXN | NO RXN | NO RXN | NO RXN |
| 307-33 | NO RXN | NO RXN | NO RXN | RXN | NO RXN | NO RXN |

As can be seen from the table, twelve of the thirty-six combinations tested result in a positive reaction. A positive reaction means that the two antibodies react with different epitopes on the same molecule.

detect and quantitate body fluid-soluble nuclear matrix proteins and protein fragments.

Dose response evaluation results of a 107.7/307.33 antibody combination is shown in Table IV, below, using ME-180 cell culture supernatant as the antigen source. The assay shows dose dependent detection of antigen in the tissue culture supernatant, demonstrating the ability of the assay to quantitate soluble interior nuclear matrix protein released from dying cells.

TABLE IV

Antibody 107-7 solid phase,
307-33 soluble antibody, ME-180 supernatant.

| Concentration of supernatant | Mean OD | SD |
|---|---|---|
| 3:1 | 0.906 | 0.009 |
| 3:2 | 0.456 | 0.011 |
| 3:4 | 0.216 | 0.007 |
| 3:8 | 0.099 | 0.005 |
| 3:16 | 0.052 | 0.002 |
| 3:32 | 0.031 | 0.005 |
| No Sup | | |

Next, interior nuclear matrix protein quantification was tested in supernatant from a variety of dying tumor tissues. Here, tumor and normal tissues were allowed to die in media as described supra. Supernatants were assayed in various configurations of sandwich assays. The results are shown in Table V, where all values are in units/gm, using ME-180 antigen as standard. As can be seen from Table V, antigen is released from each of the dying tissues, and the three assays are measuring different antigens. As expected, the increased cell death in tumor tissue is reflected in a higher average antigen value quantitated in cancer tissue versus normal tissue. In addition, significant differences in antigen quantities are seen in the different tissue sources, indicating that the soluble antigen quantities present in the supernatant vary in a cell-type specific manner.

Table VI shows the results of an analogous experiment performed using serum samples from cancer patients and normal blood donors. As for Table VI, ME-180 cell antigen was the standard. Results are reported in units/ml. A control experiment diluting supernatant antigen into serum and then quantitating the protein in solution indicates that serum has little or no effect on the assay. As can be seen in Table VI, like the results shown in Table V, serum samples from cancer patients reflect a higher rate of cell death as indicated by the quantifiably higher levels of antigen detected in these samples compared with those detected in the normal blood serum samples.

TABLE V

| | ANTIBODY COMBINATIONS | | |
|---|---|---|---|
| SAMPLE | SAMPLE # | 307-33 107-7 | 302-29 107-7 |
| NORMAL | 1 | 0.0 | 0.0 |
| NORMAL | 2 | 0.0 | 0.0 |
| NORMAL | 3 | 0.0 | 0.0 |
| NORMAL | 4 | 0.0 | 0.0 |
| NORMAL | 5 | 0.0 | 0.0 |
| NORMAL | 6 | 0.0 | 0.0 |
| NORMAL | 7 | 0.0 | 0.0 |
| NORMAL | 8 | 0.0 | 0.0 |
| NORMAL | 9 | 0.0 | 0.0 |
| NORMAL | 10 | 0.7 | 0.0 |
| NORMAL | 11 | 0.0 | 0.0 |
| NORMAL | 12 | 0.0 | 0.2 |
| NORMAL | 13 | 0.7 | 0.3 |
| NORMAL | 14 | 1.3 | 0.6 |
| NORMAL | 15 | 5.3 | 1.7 |
| NORMAL | 16 | 1.4 | 0.4 |

TABLE V-continued

| | ANTIBODY COMBINATIONS | | |
|---|---|---|---|
| SAMPLE | SAMPLE # | 307-33 107-7 | 302-29 107-7 |
| NORMAL | 17 | 2.2 | 1.0 |
| NORMAL | 18 | 2.0 | 0.0 |
| NORMAL | 19 | 3.0 | 0.4 |
| NORMAL | 20 | 2.3 | 1.3 |
| NORMAL | 21 | 3.9 | 0.6 |
| NORMAL | 22 | 8.2 | 1.3 |
| NORMAL | 23 | 4.0 | 0.8 |
| NORMAL | 24 | 4.3 | 0.7 |
| NORMAL | 25 | 9.1 | 0.6 |
| NORMAL | 26 | 5.9 | 0.2 |
| NORMAL | 27 | 20.6 | 6.0 |
| NORMAL | 28 | 2.2 | 0.7 |
| NORMAL | 29 | 5.0 | 1.0 |
| NORMAL | 30 | 3.5 | 1.2 |
| NORMAL | 31 | 10.1 | 1.0 |
| NORMAL | 32 | 3.3 | 6.3 |
| NORMAL | 33 | 1.5 | 0.0 |
| NORMAL | 34 | 6.9 | 0.8 |
| NORMAL | 35 | 0.0 | 0.0 |
| NORMAL | 36 | 1.2 | 0.0 |
| BLADDER CA | 37 | 0.0 | 0.0 |
| BLADDER CA | 38 | 1.6 | 0.0 |
| BLADDER C | 39 | 0.0 | 0.0 |
| COLON CA | 40 | 8.9 | 7.0 |
| COLON CA | 41 | 28.4 | 24.3 |
| COLON CA | 42 | 28.6 | 17.9 |
| COLON CA | 43 | 11.6 | 8.1 |
| COLON CA | 44 | 12.8 | 6.8 |
| COLON CA | 45 | 6.4 | 0.9 |
| COLON CA | 46 | 3.7 | 2.4 |
| COLON CA | 47 | 28.3 | 27.3 |
| COLON CA | 48 | 17.5 | 20.2 |
| COLON CA | 49 | 4.7 | 0.0 |
| COLON CA | 50 | 11.7 | 10.3 |
| COLON CA | 52 | 5.7 | 0.0 |
| COLON CA | 53 | 5.1 | 0.5 |
| COLON CA | 54 | 6.0 | 1.8 |
| COLON CA | 55 | 13.1 | 2.3 |
| COLON CA | 56 | 9.6 | 5.8 |
| COLOREC CA | 57 | 58.2 | 41.3 |
| ENDOMETRIUM C | 58 | 10.3 | 6.8 |
| ENDOMETRIUM C | 59 | 4.7 | 1.9 |
| ENDOMETRIUM C | 60 | 9.4 | 7.1 |
| LUNG CA | 61 | 13.4 | 9.3 |
| LUNG CA | 62 | 11.9 | 7.9 |
| LUNG CA | 63 | 19.0 | 16.2 |
| LUNG CA | 64 | 16.7 | 7.8 |
| LUNG CA | 65 | 20.8 | 11.0 |
| OVARY CA | 66 | 21.1 | 16.9 |
| OVARY CA | 67 | 16.4 | 8.9 |
| OVARY CA | 68 | 11.6 | 8.3 |
| PROSTATE CA | 69 | 12.7 | 10.8 |
| PROSTATE CA | 70 | 4.9 | 2.8 |
| PROSTATE CA | 71 | 0.0 | 3.4 |
| PROSTATE CA | 72 | 15.4 | 7.0 |
| PROSTATE CA | 73 | 0.0 | 0.0 |

TABLE VI

| TISSUE TYPE | ASSAY 1* | ASSAY 2** |
|---|---|---|
| Breast normal 90-247 | NT# | 500 |
| Breast normal 90-252 | 7574 | 2705 |
| Breast normal 90-254 | NT | 1513 |
| Breast normal 90-264 | NT | 0 |
| Breast normal 90-268 | 139 | NT |
| Breast cancer 90-256 | 438 | NT |
| Breast cancer 90-275 | 2000 | NT |
| Breast cancer 90-287 | 20222 | 7333 |
| Cervix normal 90-279 | 2500 | NT |
| Cervical cancer 90-8083 | 12666 | NT |

TABLE VI-continued

| TISSUE TYPE | ASSAY 1* | ASSAY 2** |
|---|---|---|
| Colon normal 90-253 | 1009 | NT |
| Colon cancer 90-250 | 1450 | NT |
| Kidney normal 90-259 | 4250 | NT |
| Kidney cancer 90-289 | 2407 | NT |
| Liver normal | 2154 | 614 |
| Liver normal 90-451 | NT | 131 |
| Liver cancer | 2227 | 0 |
| Met liver 90-403 | NT | 300 |
| Lung normal 90-248 | 4391 | NT |
| Lung normal 90-246 | 4200 | NT |
| Lung normal 90-107 | NT | 4166 |
| Lung normal 90-118 | NT | 650 |
| Lung cancer 90-095 | NT | 5357 |
| Lung cancer 90-121 | NT | >12000 |
| Ovarian cancer | 8621 | 6517 |
| Ovarian cancer 90-260 | 6900 | NT |
| Ovarian cancer 90-291 | 2768 | NT |
| Ovarian cancer 90-291 | NT | 10909 |
| Uterine cancer 90-277 | 6574 | NT |
| Uterus normal 90-295 | 6574 | NT |
| average normal | 3447 | 1284 |
| average cancer | 9442 | 7069 |

*Assay 1 is 107.7 solid phase and 307.33 soluble phase.
**Assay 2 is 107.7 solid phase and 302.29 soluble phase.
NT means not tested.

B. Nucleic Acid Assays

The status of a tissue also may be determined by detecting the quantity of transcripts encoding these cancer marker proteins. The currently preferred means for detecting mRNA is by means of northern blot analysis using labeled oligonucleotides e.g., nucleic acid fragments capable of hybridizing specifically with the transcript of interest. The currently preferred oligonucleotide sequence is a sequence encoding a complementary sequence to that of at least part of the transcript marker sequence. These complementary sequences are known in the art as "antisense" sequences. The oligonucleotides may be oligoribonucleotides or oligodeoxyribonucleotides. In addition, oligonucleotides may be natural oligomers composed of the biologically significant nucleotides, i.e., A (adenine), dA (deoxyadenine), G (guanine), dG (deoxyguanine), C (cytosine), dC (deoxycytosine), T (thymine) and U (uracil), or modified oligonucleotide species, substituting, for example, a methyl group or a sulfur atom for a phosphate oxygen in the inter-nucleotide phosohodiester linkage. (see, for example, Section I.C, below.) Additionally, the nucleotides themselves, and/or the ribose moieties may be modified.

The sequences may be synthesized chemically, using any of the known chemical oligonucleotide synthesis methods well described in the art. For example, the oligonucleotides are advantageously prepared by using any of the commercially available, automated nucleic acid synthesizers. Alternatively, the oligonucleotides may be created by standard recombinant DNA techniques, by, for example, inducing transcription of the noncoding strand. For example, the DNA sequence encoding a marker protein may be inverted in a recombinant DNA system, e.g., inserted in reverse orientation downstream of a suitable promoter, such that the noncoding strand now is transcribed.

Useful hybridizing oligonucleotide sequences include any sequences capable of hybridizing specifically to the MT1 or MT2 primary transcripts. Accordingly, as will be appreciated by those skilled in the art, useful sequences contemplated include both sequences complementary to the DNA sequences provided in Seq. ID No. 1 (MT1) or Seq. ID No. 2 (MT2) which correspond to the protein coding regions, as well as sequences complementary to transcript sequences occurring further upstream or downstream from the coding sequence (e.g., sequences contained in, or extending into, the 5'- and 3' untranslated regions). Representative antisense sequences are described in Seq. ID Nos. 5 and 6. Seq. ID No. 5 describes a sequence complementary to the first 100 nucleotides of the MT1 protein coding sequence (compare Seq. ID Nos. 1 and 5) as well as the 53 nucleotide sequence occurring upstream of the initiation codon. The complementary nucleotides to the initiation codon occur at positions 298–300 in Seq. ID No. 5. Similarly, Seq. ID No. 6 describes a sequence complementary to the first 100 nucleotides of the MT2 protein coding sequence (compare Seq. ID Nos. 3 and 6), as well as the 48 nucleotide sequence occurring upstream of the initiation codon. The complementary nucleotides to the initiation codon occur at positions 298–300 in Seq. ID No. 6. Useful oligomers may be created based on part or all of the sequences in Seq. ID No. 5 and 6. However, as will be appreciated by those skilled in the art, other useful sequences which hybridize to other regions of the transcript readily are created based on the sequences presented in Seq. ID Nos. 1 and 3 and/or additional, untranslated sequences, such as are disclosed for MT2 (NuMA) in Compton et al. and Yang et al.

While any length oligonucleotide may be utilized to hybridize an mRNA transcript, sequences less than 8–15 nucleotides may be less specific in hybridizing to target mRNA. Accordingly, oligonucleotides typically within the range of 8–100 nucleotides, preferably within the range of 15–50, nucleotides are envisioned to be most useful in standard RNA hybridization assays.

The oligonucleotide selected for hybridizing to the INM transcript, whether synthesized chemically or by recombinant DNA, then is isolated and purified using standard techniques and then preferably labelled (e.g., with $^{35}$S or $^{32}$P) using standard labelling protocols.

A sample containing the marker transcript of interest then is run on an electrophoresis gel, the dispersed nucleic acids transferred to a nitrocellulose filter and the labelled oligonucleotide exposed to the filter under suitable hybridizing conditions, e.g. 50% formamide, 5×SSPE, 2×Denhardt's solution, 0.1% SDS at 42° C., as described in *Molecular Cloning: A Laboratory Manual,* Maniatis et al. Other useful procedures known in the art include solution hybridization, and dot and slot RNA hybridization. The amount of marker transcript present in a sample then is quantitated by measuring the radioactivity of hybridized fragments, using standard procedures known in the art.

Following a similar protocol, oligonucleotides also may be used to identify other sequences encoding members of the MT1 and MT2 protein families, for example, as described in the examples that follow. The methodology also may be used to identify genetic sequences associated with the protein coding sequences described herein, e.g., to identify noncoding sequences lying upstream or downstream of the protein coding sequence, and which may play a functional role in expression of these genes. Where new marker species are to be identified, degenerate sequences and/or sequences with preferred codon bias may be created, using the sequences of Seq. ID Nos. 1 or 3 as templates, and the general guidelines described in the art for incorporating degeneracies. (See, for example, *Molecular Cloning: A Laboratory Manual,* Maniatis, et al.)

C. Therapeutics

The proteins described herein are associated with the spindle apparatus during mitosis, and are present at elevated levels in malignant cells. Accordingly, without being limited to any particular theory, it is hypothesized that the proteins likely play a significant role in cell division, most likely a structurally related role. Accordingly, these proteins and their transcripts are good candidates as target molecules for a cancer chemotherapy.

C.1 Antisense Therapeutics

A particularly useful cancer therapeutic envisioned is an oligonucleotide complementary to part all of the marker transcript, capable of hybridizing specifically to the transcript and inhibiting translation of the mRNA when hybridized to the mRNA transcript. Antisense oligonucleotides have been used extensively to inhibit gene expression in normal and abnormal cells. See, for example, Stein et al. (1988) Cancer Res. 48:2659–2668, for a pertinent review of antisense theory and established protocols. Accordingly, the antisense nucleotides to MT1 and MT2 may be used as part of chemotherapy, alone or in combination with other therapies.

As described in Section I.B above, both oligoribonucleotide and oligodeoxyribonucleotide sequences will hybridize to an mRNA transcript and may be used to inhibit mRNA translation of the marker protein described herein. However, oligoribonucleotides generally are more susceptible to enzymatic attack by ribonucleases than deoxyribonucleotides. Hence, oligodeoxyribonucleotides are preferred for in vivo therapeutic use to inhibit mRNA translation in an individual.

Also, as described in Section I.B above, the therapeutically useful antisense oligonucleotides of the invention may be synthesized by any of the known chemical oligonucleotide synthesis methods well described in the art. Alternatively, a complementary sequence to part or all of the natural mRNA sequence may be generated using standard recombinant DNA technology. For example, the DNA encoding the protein coding sequence may be inserted in reverse orientation downstream of a promoter capable of expressing the sequence such that the noncoding strand is transcribed.

Since the complete nucleotide sequence of the protein coding sequence as well as additional 5' and 3' untranslated sequences are known for both MT1 and MT2 (see, for example, Seq. ID Nos. 1 and 3 and Compton et al.), and/or can be determined with this disclosure, antisense oligonucleotides hybridizable with any portion of the mRNA transcripts to these proteins may be prepared using conventional oligonucleotide synthesis methods known to those skilled in the art.

Oligonucleotides complementary to and hybridizable with any portion of the MT1 and MT2 mRNA transcripts are, in principle, effective for inhibiting translation of the transcript as described herein. For example, as described in U.S. Pat. No. 5,098,890, issued Mar. 24, 1992, the disclosure of which is incorporated herein by reference, oligonucleotides complementary to mRNA at or near the translation initiation codon site may be used to advantage to inhibit translation. Moreover, it has been suggested that sequences that are too distant in the 3' direction from the translation initiation site may be less effective in hybridizing the mRNA transcripts because of potential ribosomal "read-through", a phenomenon whereby the ribosome is postulated to unravel the antisense/sense duplex to permit translation of the message.

Representative antisense sequences for MT1 and MT2 transcripts are described in Seq. ID No. 5 (MT1) and Seq. ID No. 6 (MT2). The antisense sequences are complementary the sequence encoding the N-terminus of either the MT1 or MT2 marker protein, as well as part of the 5' untranslated sequences immediately upstream of the initiation codon. (See Section I.B, above for a detailed description of these sequences). As will be appreciated by those skilled in the art, antisense oligonucleotides complementary to other regions of the MT1 and/or MT2 transcripts are readily created using for example, the sequences presented in Seq. ID No. 1 and 3 as templates.

As described in Section I.B above, any length oligonucleotide may be utilized to hybridize to mRNA transcripts. However, very short sequences (e.g., less than 8–15 nucleotides) may bind with less specificity. Moreover, for in vivo use such short sequences may be particularly susceptible to enzymatic degradation. In addition, where oligonucleotides are to be provided directly to the cells, very long sequences may be less effective at inhibition because of decreased uptake by the target cell. Accordingly, where the oligonucleotide is to be provided directly to target cells, oligonucleotides having a length within the range of 8–50 nucleotides, preferably 15–30 nucleotides, are envisioned to be most advantageous.

An alternative means for providing antisense sequences to a target cell is as part of a gene therapy technique, e.g., as a DNA sequence, preferably part of a vector, and associated with a promoter capable of expressing the antisense sequence, preferably constitutively, inside the target cell. Recently, Oeller et al. ((1992) Science 254:437–539, the disclosure of which is in corporated by reference) described the in vivo inhibition of the ACC synthase enzyme using a constitutively expressible DNA sequence encoding an antisense sequence to the full length ACC synthase transcript. Accordingly, where the antisense sequences are provided to a target cell indirectly, e.g., as part of an expressable gene sequence to be expressed within the cell, longer oligonucleotide sequences, including sequences complementary to substantially all the protein coding sequence, may be used to advantage.

Finally, also as described in Section I.B, above, the therapeutically usefully oligonucleotides envisioned include not only native oligomers composed of naturally occurring nucleotides, but also those comprising modified nucleotides to, for example, improve stability and lipid solubility and thereby enhance cellular uptake. For example, it is known that enhanced lipid solubility and/or resistance to nuclease digestion results by substituting a methyl group or sulfur atom for a phosphate oxygen in the internucleotide phosphodiester linkage. Phosphorothioates ("S-oligonucleotides" wherein a phosphate oxygen is replaced by a sulfur atom), in particular, are stable to nuclease cleavage, are soluble in lipids, and are preferred, particularly for direct oligonucleotide administration. S-oligonucleotides may be synthesized chemically by the known automated synthesis methods described in Section I.B, above.

Suitable oligonucleotide sequences for mRNA translation inhibition are readily evaluated by a standard in vitro assay using standard procedures described herein and well characterized in the art. An exemplary protocol is described below, but others are envisioned and may be used to advantage.

A candidate antisense sequence is prepared as provided herein, using standard chemical techniques. For example, an MT1 antisense sequence may be prepared having the sequence described by positions 285–315 of Sequence ID No. 5 using an Applied Biosystems automated DNA Synthesizer, and the oligonucleotide purified accordingly to manufacturer's instructions. The oligonucleotide then is provided to a suitable malignant cell line in culture, e.g., ME-180, under standard culture conditions, to be taken up by the proliferating cells.

Preferably, a range of doses is used to determine effective concentrations for inhibition as well as specificity of hybridization. For example, a dose range of 0–100 μg oligonucleotide/ml may be assayed. Further, the oligonucleotides may be provided to the cells in a single transfection, or as part of a series of transfections.

Antisense efficacy may be determined by assaying a change in cell proliferation over time following transfection, using standard cell counting methodology and/or by assaying for reduced expression of marker protein, e.g., by immunofluorescence, as described in Section I.A, above. Alternatively, the ability of cells to take up and use thymidine is another standard means of assaying for cell division and maybe used here, e.g., using $^3$H thymidine. Effective antisense inhibition should inhibit cell division sufficiently to reduce thymidine uptake, inhibit cell proliferation, and/or reduce detectable levels of marker proteins.

Useful concentration ranged are envisioned to vary according to the nature and extent of the neoplasm, the particular oligonucleotide utilized, the relative sensitivity of the neoplasm to the oligonucleotides, and other factors. Useful ranges for a given cell type and oligonucleotide may be determined by performing a standard dose range experiment as described here. Dose range experiments also may be performed to assess toxicity levels for normal and malignant cells. Concentrations from about 1 to 100 μg/ml per $10^5$ cells may be employed to advantage.

For in vivo use, the antisense oligonucleotides may be combined with a pharmaceutical carrier, such as a suitable liquid vehicle or excipient and an optional auxiliary additive or additives. The liquid vehicles and excipients are conventional and commercially available. Illustrative thereof are distilled water, physiological saline, aqueous solutions of dextrose, and the like. For in vivo cancer therapies, the antisense sequences preferably are provided directly to the malignant cells, as by injection to the neoplasm locus. Alternatively, the oligonucleotide may be administered systemically, provided that the antisense sequence is associated with means for directing the sequences to the target malignant cells.

In addition to administration with conventional carriers, the antisense oligonucleotides may be administered by a variety of specialized oligonucleotide delivery techniques. For example, oligonucleotides maybe encapsulated in liposomes, as described in Maniatis et al., Mannino et al. (1988) *BioTechnology* 6:682, and Felgner et al. (1989) *Bethesda Res. Lab. Focus* 11:21. Reconstituted virus envelopes also have been successfully used to deliver RNA and DNA to cells. (see, for example, Arad et. al., (1986) *Biochem. Biophy. Acta.* 859, 88–94.)

For therapeutic use in vivo, the antisense oligonucleotides are provided in a therapeutically effective amount, e.g., an amount sufficient to inhibit target protein expression in malignant cells. The actual dosage administered may take into account whether the nature of the treatment is prophylactic or therapeutic in nature, the age, weight, health and sex of the patient, the route of administration, the size and nature of the malignancy, as well as other factors. The daily dosage may range from about 0.01 to 1,000 mg per day. Greater or lesser amounts of oligonucleotide may be administered, as required. As will be appreciated by those skilled in the medical art, particularly the chemotherapeutic art, appropriate dose ranges for in vivo administration would be routine experimentation for a clinician. As a preliminary guideline, effective concentrations for in vitro inhibition of the target molecule may be determined first, as described above.

II.B Protein Inhibition

In another embodiment, the cancer marker protein itself may be used as a target molecule. For example, a binding protein designed to bind the marker protein essentially irreversibly can be provided to the malignant cells e.g., by association with a ligand specific for the cell and known to be absorbed by the cell. Means for targeting molecules to particular cells and cell types are well described in the chemotherapeutic art.

Binding proteins maybe obtained and tested as described in Section I.A above. For example, the binding portions of antibodies maybe used to advantage. Particularly useful are binding proteins identified with high affinity for the target protein, e.g., greater than about $10^9$ $M^{-1}$. Alternatively, the DNA encoding the binding protein may be provided to the target cell as part of an expressable gene to be expressed within the cell following the procedures used for gene therapy protocols well described in the art. (see, for example, U.S. Pat. No. 4,497,796, and *Gene Transfer,* Vijay R. Baichwal, ed., (1986). It is anticipated that the complexed INM protein will be disabled and can inhibit cell division thereby.

As described above for antisense nucleotides, for in vivo use, suitable binding proteins may be combined with a suitable pharmaceutical carrier, such as physiological saline or other useful carriers well characterized in the medical art. The pharmaceutical compositions may be provided directly to malignant cells, e.g., by direct injection, or may be provided systemically, provided the binding protein is associated with means for targeting the protein to target cells. Finally, suitable dose ranges and cell toxicity levels may be assessed using standard dose range experiments. Therapeutically effective concentrations may range from 0.1–1,000 mg per day. As described above, actual dosages administered may vary depending, for example, on the nature of the malignanacy, the age, weight and health of the individual, as well as other factors.

II. Exemplification

The following examples further describe how the genetic sequences encoding MT1 and MT2 proteins were isolated and characterized, including the current best mode for their cloning and characterization, without limiting the scope thereof. For example, INM protein expression in *E. coli* is described herein. However, other prokayrotic and eukaryotic cell expression systems also are contemplated for recombinant expression of the proteins described herein. Other useful hosts contemplated include Saccharomyces, the insect/baculovirus expression system, and mammalian cells such as xenogenic myeloma cells and the well-characterized chinese hamster ovary cell lines.

MT1

As described in co-pending application Ser. No. 785,804, MT1 expression levels are enhanced significantly in carcinoma cells as determined by body fluid assays performed on cultured cervical tumor cell lines (Me-180 and CaSki, ATCC, Rockville, Md.).

The natural-sourced MT1 protein first was separated from human cervical tumor cells essentially following the procedure of Penman and Fey described in U.S. Pat. Nos. 4,882, 268 and 4,885,236. Cells from the human cervical tumor cell lines CaSki and ME180 (obtained from the American Tissue Culture Collection, ATCC, Rockville, Md.) were grown to confluence and removed from flasks by trypsinization. Suspended cells were washed twice with phosphate buffered saline (PBS) and extracted with cytoskeletal buffer (CSK): 100 mM NaCl, 300 mM sucrose, 10 mM PIPES, 3 mM MgCl$_2$, 1 mM EGTA, 0.5% Triton X-100, 1.2 mM PMSF for 1 min at 4° C., followed by extraction in cold RSB (reticulocyte suspension buffer)/double detergent buffer:

100 mM NaCl, 3 mM MgCl$_2$, 10 mM Tris, pH 7.4, 1% Tween 40, 0.5% deoxycholate, 1.2 mM PMSF. Alternatively, cells were extracted twice with the RBS/double detergent buffer. The two extraction protocols produced very similar preparations. The extracted cells were digested for 30 min at room temperature in digestion buffer: 50 mM NaCl, 300 mM sucrose, 0.5% Triton X-100, 10 mM PIPES (pH 6.8), 3 mM MgCl$_2$, 1 mM EGTA, 1.2 mM PMSF, containing 100 μg of both RNase A and DNase I. Chromatin was extracted from the digested nuclei by the addition of 2M ammonium sulfate to a final concentration of 0.25M. The extracted nuclear matrix-intermediate filament (NM-IF) scaffolds then were sedimented at 3700×g for 15 min.

The resulting pellet then was resuspended in disassembly buffer: 8M urea, 20 mM MES (pH 6.6), 1 mM EGTA, 1.2 mM PMSF, 0.1 mM MgCl$_2$, 1% 2-mercaptoethanol, and the pellet sonicated and dialyzed overnight with 3 changes of 2000 volumes of assembly buffer: 0.15M KCl,25 mM imidazole (pH 7.1), 5 mM MgCl$_2$, 2 mM DTT, 0.125 mM EGTA, 0.2 mM PMSF. The dialysate then was centrifuged at 100 k×g for 1 h and the NM proteins recovered from the supernatant. Alternatively, NM-IF scaffolds were extracted directly with E400 buffer: 0.4M NaCl, 0.02M Tris pH 7.5, 0.1 mM MCl$_2$, 0.5% 2-mercaptoethanol, 1.2 mM PMSF, for 30 min at 4° C., as described by von Kries et al. (1991) *Cell* 64:123–135. The intermediate filament-rich pellet then was removed after centrifugation for 90 min at 40K rpm in a Beckman 70.1 Ti rotor. The supernatant remaining is enriched in MT1 protein with little cytokeratin contamination.

MT1-specific antibodies were produced by standard procedures. Specifically, Balb/c by J mice (Jackson Laboratory, Bar Harbor, Me.) were injected intraperitoneally with purified Caski NM protein every 2 weeks for a total of 16 weeks. The mice were injected with a single boost 4 days prior to sacrifice and removal of the spleen. Freund's complete adjuvant was used in the first injection, incomplete Freund's in the second injection; subsequent injections were made with saline. Spleen cells were fused with the SP2/O-Ag14 mouse myeloma line (ATCC, Rockville, Md.) using the standard fusion methodologies well known in the art. Hybridomas producing antibodies that reacted with nuclear matrix proteins were cloned and grown as ascites. MT1 specificity was assessed both by immunoflourescence spectroscopy and Western blot analysis.

The cDNA clones for MT1 were obtained from a Lambda ZAP expression library (Stratagene, La Jolla, Calif.). Library screening was carried out according to the manufacturer's instructions. Briefly, a single positive clone containing a 2.45 kb insert was identified and subcloned into pBluescript II vectors (Stratagene, La Jolla, Calif.) opened at the EcoRI and XhoI cloning sites. The resulting plasmid, pMT1, was sequenced directly and further subcloned to produce the MT1 fusion protein (see below).

The cDNA sequences were obtained using the standard dideoxy method described in the art. Double stranded sequencing was done utilizing the pMT1 vector primed with appropriate primers according to manufacturer's instructions (Stratagene, La Jolla, Calif.). Internal sequences were obtained using synthetic primers, created based on the identified sequence.

The entire nucleotide sequence and predicted amino acid sequence for MT1 are shown in Seq. ID No. 1. The cDNA clone retains a polyadenylation signal a putative initiation codon, a continuous open reading frame and codon utilization consistent with a human gene. The predicted amino acid sequence of MT1 consists of 639 amino acids encoding a protein of 70.5 kD with a pI of 5.47. The primary structure, as predicted by the Chou-Fasman algorithm (Chou and Fasman, (1978) *Adv. Enzymol. Relat. Areas Mol. Biol.* 47:145–148), consists of 72% alpha helix of which 56% is extended helix.

The primary structure of MT1, represented in FIG. 1, contains 27 proline residues which generally occur in pairs or triplets throughout the molecule. The proline distribution within the sequence is illustrated in FIG. 1A, where diamonds represent the proline residues. Proline pairs and triplets are indicted by stacked diamonds. At the N terminus, a 40 amino acid stretch contains a cluster of 8 prolines (residues 42–81, Seq. ID No. 1) that occur as pairs separated by 3 or fewer amino acids. A similar proline-rich region occurs in the C terminus of MT1 (residues 551–563) where 6 prolines occur in a 13 amino acid stretch. Both proline-rich regions likely lie on the protein surface, based on probability calculations determined by the technique of Emini et al. (1985) *J. Virol.* 55:836–839. The high proline density also may explain the anomalous apparent molecular weight of the protein as determined by SDS polyacrylamide gel electrophoresis. As described above, the predicted molecular weight for MT1, calculated from the amino acid sequence, is 70.1 kD. However, as described below, both the natural-sourced and recombinant protein migrate as a 90 kD protein on an SDS polyacrylamide gel. Alternatively, it is also possible that the molecular weight variation may result from some post-translational modification achievable in both prokaryotic and eukaryotic cells.

Between the two proline-rich termini, MT1 displays a sequence consistent with a region of extended alpha helix structure, indicated by the hatched structure in FIG. 1B. The extended helix is interrupted in 4 places by short helix-distorting amino acid stretches that usually include a pair of proline residues. A preliminary hypothesis as to the structure of MT1 based on these theoretical calculations is that the molecule consists of an extended rod that is bounded on either end by a globular, proline-rich domain.

Analysis of all available sequence databases indicates that MT1 has a novel sequence that bears no significant homology to any known protein. In addition, the sequence appears to lack any known, identifiable DNA binding motif such as the leucine zipper motif.

The cloned MT1 DNA was used to perform standard Northern blot analysis of total and poly A+ RNA from ME180 cells, using standard procedures and 15 μg RNA. After blotting and hybridization with $^{32}$P-labelled pMT1 DNA, a single mRNA band was detected in the poly A+ fraction. This band was not apparent in the total RNA lane after a 48 h exposure of the autoradiogram, indicating that the MT1 message is a low abundance species. Northern blot analysis indicates that the MT1 protein is translated from a single mRNA. Northern blot analysis also indicates that the MT1 RNA includes approximately 500 bp 5' of the protein-coding sequence presented in Seq. ID No. 1. This upstream sequence may represent one or more untranslated sequences and/or may encode additional protein coding sequences.

A fusion protein for MT1 was obtained using the insert from the pMT1 construct described above and in Seq. ID No. 1, and the pMAL expression system (New England Biolabs Inc., Beverly, Mass.). In this system the gene of interest (MT1) is cloned into the pMal-c vector (New England Biolabs Inc., Beverly, Mass.) and the vector transfected into *E. coli* and expressed to produce a fusion protein containing both the protein of interest and the maltose binding protein. The maltose binding protein allows the fusion protein to be selectively purified in the presence of maltose and can be subsequently cleaved by proteolytic clavage with Factor Xa to yield intact, recombinant MT1 protein. Here, MT1 cDNA was cloned into the pMAL-c vector such that the initiation AUG codon was directly continuous with the 5' terminus of the maltose binding protein. After proteolytic cleavage with factor Xa the resulting MT1 fusion protein retains the complete amino acid sequence encoded by the MT1 cDNA with no additional amino acids. All experimental details of the pMAL system were carried out according to the manufacturer's instructions.

As described above, both the natural-sourced and recombinantly produced protein have an electrophoretic mobility consistent with an apparent molecular weight of about 90 kD on SDS-PAGE. In addition, the pI of both proteins is equivalent (5.4) and consistent with the predicted pI as calculated from the amino acid sequence. Peptide mapping of both proteins by cleavage at cysteine residues with 2-nitro-5-thiocyanobenzoic acid (NTCB), following the method of Leto and Marchesi (1984) *J. Biol. Chem.* 259:4603–4049, yields equivalent peptide fragments which share the same MT1 cross reactivity by Western blot analysis. Moreover, the number and size of the peptide fragments produced are consistent with those predicted from the proposed MT1 amino acid sequence.

MT2

Like MT1, MT2 expression levels are enhanced significantly in malignant cells, as determined by serum assays.

Following the same general procedure as for MT1, a composition selectively enriched for MT2 was obtained from ME-180 cells (cervical carcinoma cells, from ATCC, Rockville, Md.), and MT2-specific antibodies prepared. These antibodies then were used to obtained a partial cDNA clone for MT2, by screening a lambda ZAP expression library, as for MT-1. The partial clone retrieved then was subcloned into a pBluescript II vector (pMT2) and the MT2 cDNA sequenced using standard techniques. The sequenced DNA, which corresponds to residues 1366 to 2865 of Seq. ID No. 3, then was analyzed to determine the reading frame and encoded amino acid sequence. The complete coding sequence subsequently was determined and is presented in Seq. ID No. 3. (Compton et al. (1992) *J. Cell Biol.* 116: 1395–1408). The nucleotide sequence and predicted amino acid sequence for MT2 are described in Seq. ID No. 3.

The primary structure of MT2 is represented schematically in FIG. 2: The protein appears to comprise at least 6 helical regions separated by proline pairs, (See FIGS. 2A and B.) The primary structure may allow the protein to form a coiled-coil structure in solution. As for FIG. 1, prolines are indicated by diamonds and helices by hatched boxes. In addition, both the N and C termini of MT2 appear to fold as globular domains (Compton et al. (1992) *J. Cell Biol.* 116: 1395–1408.)

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method of detecting the presence of a malignancy in a mammal, the method comprising the steps of:

(a) contacting a sample from said mammal with an antibody or an antigen binding domain thereof that binds specifically to a marker protein for said malignancy, said marker protein comprising the amino acid sequence of SEQ ID NO:4 or a variant thereof, wherein said variant is characterized as being encoded by a nucleic acid sequence that hybridizes under stringent hybridization conditions with a nucleic acid sequence complementary to the nucleic acid of SEQ ID NO:3 and having an amino acid sequence which binds specifically to an immunoglobulin that binds specifically to the amino acid sequence encoded by the nucleic acid sequence of SEQ ID NO:3; and (b) detecting in the sample the presence of said marker protein or a fragment thereof bound by the antibody or the antigen binding domain thereof, wherein the presence of said marker protein or said fragment is indicative of the presence of said malignancy in said mammal.

2. The method of claim 1 wherein said marker protein comprises amino acid residues 456–955 of SEQ ID NO:4.

3. The method of claim 1 wherein said malignancy is a cancer selected from the group consisting of breast, bladder, lung, prostate, ovarian, cervical, colon and colorectal cancer.

4. The method of claim 1 wherein said malignancy is a colon cancer.

5. The method of claim 1 wherein said malignancy is a bladder cancer.

6. The method of claim 1 wherein said malignancy is a cervical cancer.

7. The method of claim 1 wherein the antibody or the antigen binding domain thereof has a binding affinity for said marker protein greater than $10^5$ $M^{-1}$.

8. The method of claim 7 wherein the antibody or the antigen binding domain thereof has a binding affinity for said marker protein greater than $10^7$ $M^{-1}$.

9. The method of claim 1 wherein the sample comprises a body fluid.

10. The method of claim 9 wherein the body fluid is selected from the group consisting of serum, plasma, blood, urine, semen, vaginal secretions, spinal fluid, ascitic fluid, and peri toneal fluid.

11. The method of claim 9 wherein the body fluid is serum.

12. The method of claim 9 wherein the body fluid is urine.

13. The method of claim 4 wherein the sample is serum.

14. The method of claim 5 wherein the sample is urine.

15. The method of claim 1 comprising the additional step of quantitating the abundance of said marker protein or said fragment thereof in the sample, wherein an elevated level of said marker protein or said fragment thereof compared to normal is further indicative of the presence of said malignancy in said mammal.

16. A method of detecting a cancer in an individual, the method comprising the steps of:
  (a) contacting a body fluid sample drawn from the individual with an antibody or an antigen binding domain thereof that binds specifically to a marker protein for said cancer, said marker protein comprising the amino acid sequence of SEQ ID NO:4 or a variant thereof, wherein said variant is characterized as being encoded by a nucleic acid sequence that hybridizes under stringent hybridization conditions with a nucleic acid sequence complementary to the nucleic acid of SEQ ID NO:3 and having an amino acid sequence which binds specifically to an immunoglobulin that binds specifically to the amino acid sequence encoded by the nucleic acid sequence of SEQ ID NO:3;
  (b) measuring in the sample the quantity per unit volume of said marker protein or a fragment thereof bound by the antibody or the antigen binding domain thereof; and
  (c) comparing the quantity per unit volume of said marker protein or said fragment thereof with a mean value indicative of a patient without said cancer, wherein a quantity per unit volume of said marker protein or said fragment thereof in the sample greater than the mean value is indicative of the presence of said cancer in the individual.

17. The method of claim 16, wherein said marker protein comprises amino acid residues 456–955 of SEQ ID NO:4.

18. The method of claim 16 wherein said cancer is selected from the group consisting of breast, bladder, lung, prostate, ovarian, cervical, colon and colorectal cancer.

19. The method of claim 16 wherein said cancer is a colon cancer.

20. The method of claim 16 wherein said cancer is a bladder cancer.

21. The method of claim 16 wherein said cancer is a cervical cancer.

22. The method of claim 16 wherein the antibody or the antigen binding domain thereof has a binding affinity for said marker protein greater than $10^5$ $M^{-1}$.

23. The method of claim 22 wherein the antibody or the antigen binding domain thereof has a binding affinity for said marker protein greater than $10^7$ $M^{-1}$.

24. The method of claim 16 wherein the sample is selected from the group consisting of serum, plasma, blood, urine, semen, vaginal secretions, spinal fluid, ascitic fluid, and peritoneal fluid.

25. The method of claim 16 wherein the sample is serum.

26. The method of claim 16 wherein the sample is urine.

27. The method of claim 19 wherein the sample is serum.

28. The method of claim 20 wherein the sample is urine.

* * * * *